US007056901B2

(12) United States Patent
Frechet et al.

(10) Patent No.: US 7,056,901 B2
(45) Date of Patent: Jun. 6, 2006

(54) MICROGEL PARTICLES FOR THE DELIVERY OF BIOACTIVE MATERIALS

(75) Inventors: Jean M. J. Frechet, Oakland, CA (US); Niren Murthy, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/401,496

(22) Filed: Mar. 28, 2003

(65) Prior Publication Data

US 2003/0211158 A1 Nov. 13, 2003

Related U.S. Application Data

(60) Provisional application No. 60/368,576, filed on Mar. 29, 2002.

(51) Int. Cl.
*A61K 48/00* (2006.01)
*A61K 37/715* (2006.01)
*A61K 39/00* (2006.01)
*A61K 9/14* (2006.01)

(52) U.S. Cl. ............................ 514/54; 514/58; 514/59; 514/44; 424/486; 424/488; 424/184.1; 435/69.1; 435/6; 530/350; 536/23.1; 536/23.4

(58) Field of Classification Search ................. 514/54, 514/58, 59, 44; 424/486, 488, 184.1; 435/69.1, 435/6; 530/350; 536/23–1, 23.4
See application file for complete search history.

(56) References Cited

U.S. PATENT DOCUMENTS

| 5,191,015 A | 3/1993 | Sheppard et al. |
| 5,529,777 A | 6/1996 | Andrianov et al. |
| 5,783,567 A | 7/1998 | Hedley et al. |
| 5,869,103 A | 2/1999 | Yeh et al. |
| 6,306,405 B1 | 10/2001 | O'Hagan et al. |
| 6,306,922 B1 | 10/2001 | Hubbell et al. |
| 6,312,731 B1 | 11/2001 | Staas et al. |
| 6,333,051 B1 * | 12/2001 | Kabanov et al. ............ 424/484 |
| 6,534,064 B1 | 3/2003 | O'Hagan et al. |
| 2002/0045582 A1 | 4/2002 | Margolin et al. |

OTHER PUBLICATIONS

Ruckenstein et al., Macromolecules, 32, 3979-3983, 1999.*
Dijk-Wolthuis et al., Macromolecules, 30, 4639-4645, 1997.*
Anseth et al., "Photopolymerizable degradable polyanhydrides with osteocompatibility" *Nature Biotechnology* 17:156-159 (Feb. 1999).
Anseth et al., "In situ forming degradable networks and their application in tissue engineering and drug delivery," *J. of Controlled Release* 78 (2002) 199-209.

(Continued)

*Primary Examiner*—James O. Wilson
*Assistant Examiner*—Devesh Khare
(74) *Attorney, Agent, or Firm*—Michelle S. Chew; Lawrence Berkeley National Laboratory

(57) ABSTRACT

Novel microgels, microparticles and related polymeric materials capable of delivering bioactive materials to cells for use as vaccines or therapeutic agents. The materials are made using a crosslinker molecule that contains a linkage cleavable under mild acidic conditions. The crosslinker molecule is exemplified by a bisacryloyl acetal crosslinker. The new materials have the common characteristic of being able to degrade by acid hydrolysis under conditions commonly found within the endosomal or lysosomal compartments of cells thereby releasing their payload within the cell. The materials can also be used for the delivery of therapeutics to the acidic regions of tumors and sites of inflammation.

17 Claims, 17 Drawing Sheets

OTHER PUBLICATIONS

Behravesh et al, "Synthesis of in Situ Cross-Linkable Macroporous Biodegradable Poly(propylene fumarate-co-ethylene glycol) Hydrogels", *Biomacromolecules* 3, 374-381 (Feb. 6, 2002).

Daubreese et al., "Synthesis and Inverse Emulsion Polymerization of Aminated Acrytamidodextran," *J. Pharm. Pharmacol*, 45, 1018-1023 (1993).

Delgado et al, "A Tunable Hydrogel for Encapsulation and Controlled Release of Bioactive Proteins", *Biomacromolecules* 3, 262-271 (Dec. 21, 2001).

Helmlinger et al., "Acid Production in Glycolysis-impaired Tumors Provides New Insights into Tumor Metabolism," *Clin. Cancer Res.* vol. 8, 1284-1291, Apr. 2002.

Hoffman, "Hydrogels for Biomedical Applications", *Annals of the NY Academy of Sciences* 944:62-73 (2001).

Lu et al., Release Behavior of High Molecular Weight Solutes from Poly(ethylene glycol)- Based Degradable Networks. (2000) *Macromolecules*, 33, 2509-2515.

Lynn et al., "pH-Responsive Polymer Microspheres: Rapid Release of Encapsulated Material within the Range of intracellular pH," *Angrew. Chem., Int Ed.* 2001, 40, 1707-1710.

Murthy et al "A Novel Strategy for Encapsulation and Release of Proteins: Hydrogels and Microgels with Acid-Labile Acetal Cross-Linkers," *J. Am. Chem. Soc.* 2002, 124, 12398-12399.

O'Hagan et al. (1998) Poly(lactide-co-glycolide) microparticles for the development of single-dose controlled-release vaccines, *Adv. Drug Deliv. Rev.* 32, 225-246.

Park, "Temperature modulated protein release from pH/temperature-sensitive hydrogels", Biomaterials 20 (1999) 517-521.

Park et al., "Controlled release of clot-dissolving tissue-type plasminogen activator from a poly(L-glutamic acid) semi-interpenetrating polymer network hydrogel," J. of Controlled Release 75 (2001) 37-44.

Ruckenstein et al. (May 7, 1999) A Novel Breakable Cross-linker and pH-Responsive Star-Shaped and Gel Polymers, *Macromolecules*. 32, 3979-3983.

Sassi et al., "Partitioning of proteins and small biomolecules in temperature- and pH-sensitive hydrogels," *J. M. Polymer*, 11, 2151-2164 (1996).

Sawhney et al. (1993) Bioerodible hydrogels based on photopolymerized poly(ethyleneglycol)-co-poly($\alpha$-hydroxy acid) Diacrylate Macromers. *Macromolecules*, 26, 581-587.

Trevani et al. "Extracellular Acidification Induces Human Neutrophil Activation". *J. of Immunology*, 1999, 162: 4849-4857.

Van Dijk-Wolthius et al. (1997) "Degradation and Release Behavior of Dextran Based Hydrogels". *Macromolecules*. 30, 4639-4645.

* cited by examiner

FIG. 2

Generic Formula for Crosslinker:

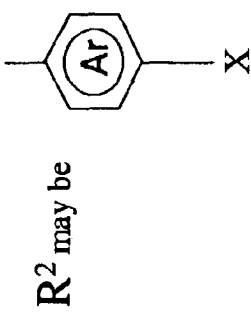

Compound I $R^1$ represents two groups that may be the same or different, selected from:

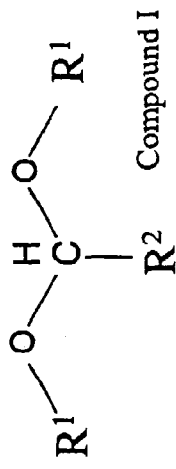

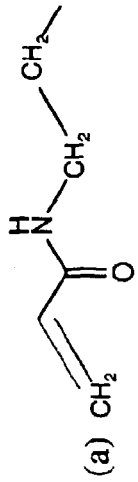

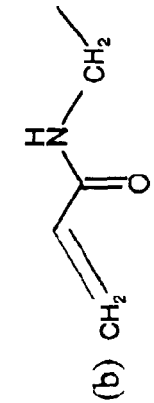

X = F, Br, Cl, or I

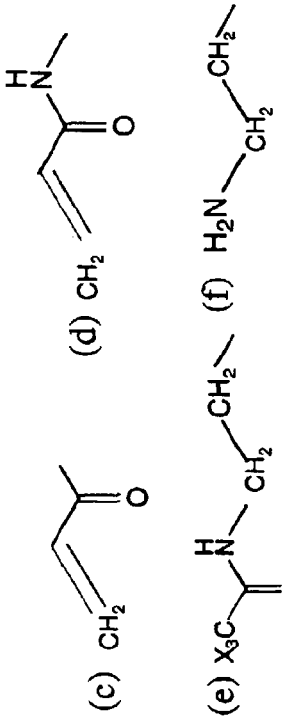

$R^2$ may be

Ar = phenyl, napthyl or substituted aryl

X = methoxy, dimethyl amine, H,
—O—[CH$_2$—CH$_2$—O]$_n$—CH$_3$, (where n = 2-10) polyethylene glycol of MW 300-3000,
—O—CH$_2$—CH$_2$—O—C(O)—O—Ph—NO$_2$, or
—O—CH$_2$—CH$_2$—NH—CO—dextran polysaccharide (dextran polysaccharide of MW up to 100,000)

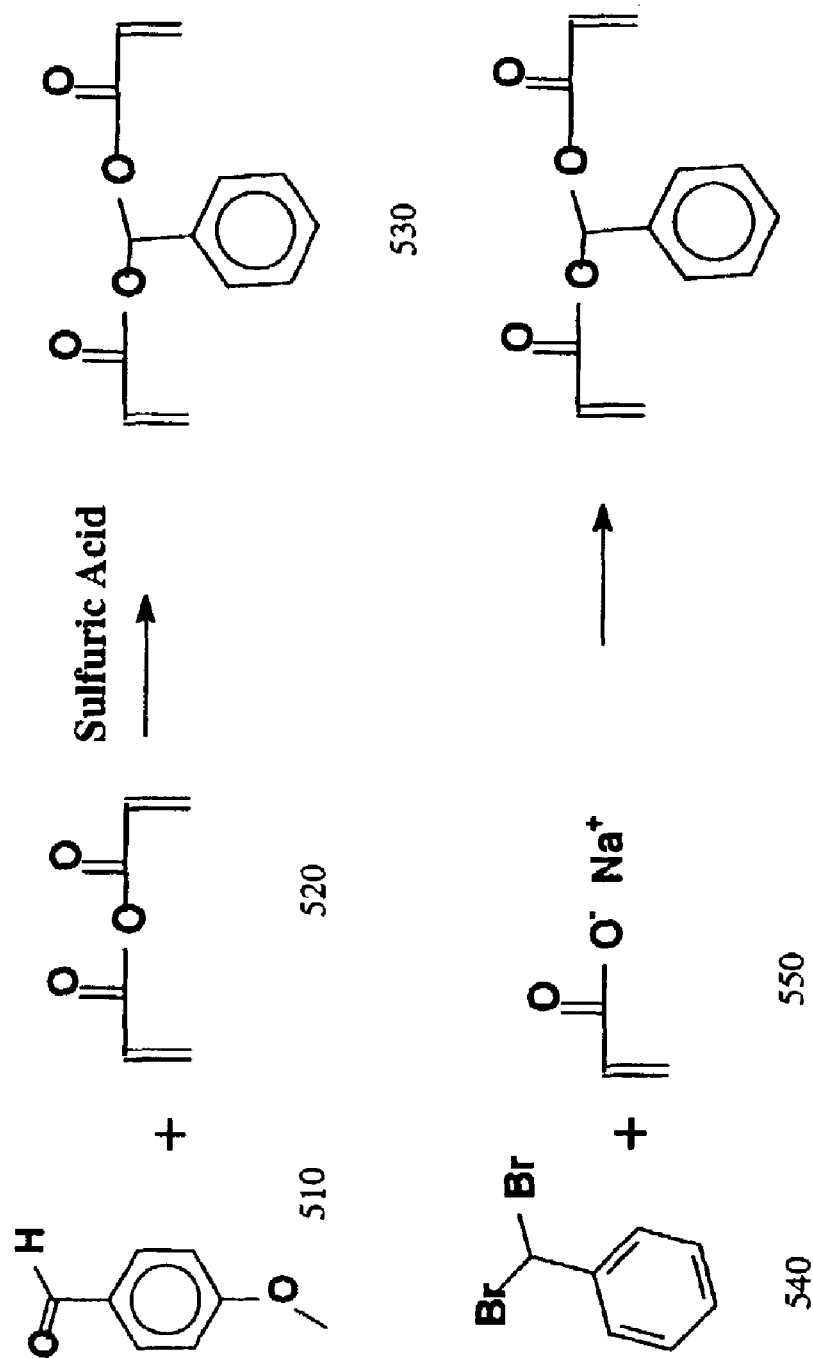

FIG. 9D
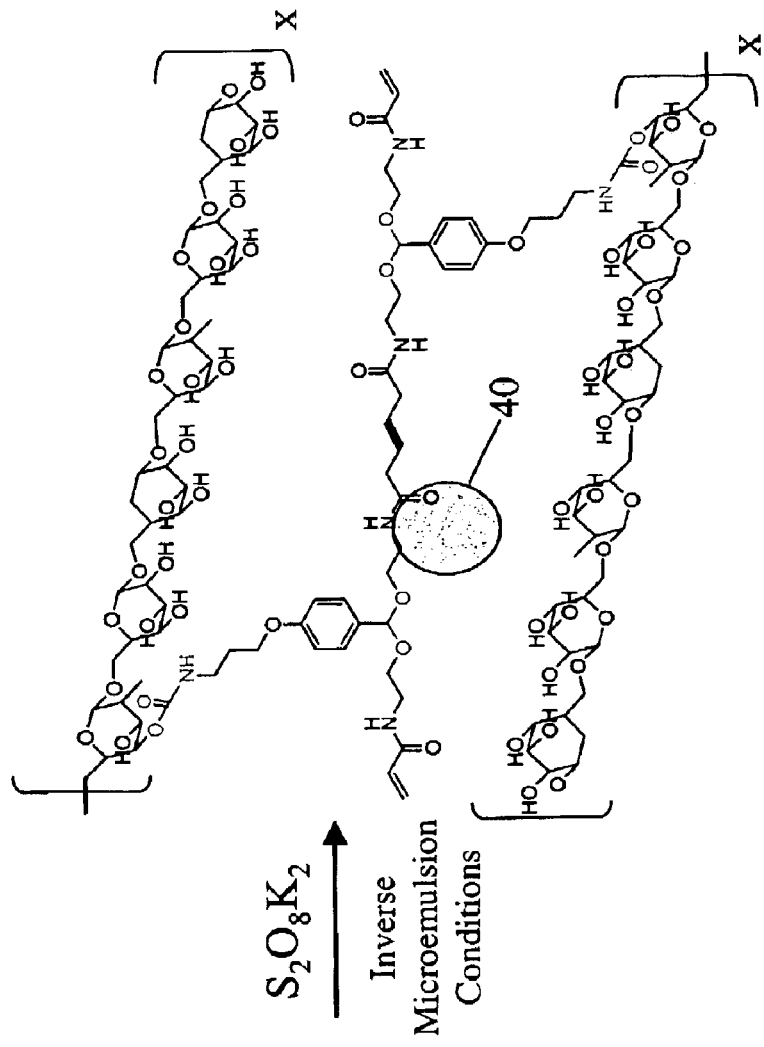
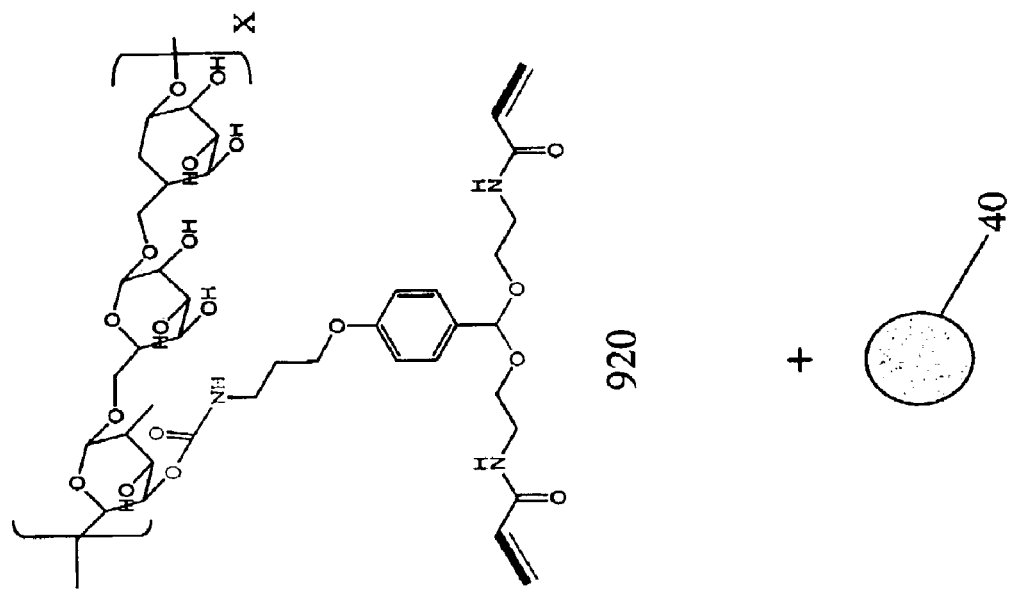

MICROGEL PARTICLES FOR THE DELIVERY OF BIOACTIVE MATERIALS

CROSS-REFERENCE TO RELATED APPLICATIONS

This application claims priority to U.S. Provisional Patent Application No. 60/368,576, which was filed on Mar. 29, 2002, which is incorporated by reference in its entirety.

STATEMENT OF GOVERNMENT SUPPORT

This invention was made during work partially supported by the U.S. Department of Energy under Contract No. DE-AC03-76SF00098. The government has certain rights in this invention.

BACKGROUND OF THE INVENTION

1. Field of the Invention

This invention generally relates to the field of cross-linked hydrogel polymers formed into microgels for use in delivery of bioactive materials such as antigens, DNA and other therapeutics.

2. Description of the Related Art

There is a great need for the development of vaccines against AIDS, Hepatitis C, cancer and other diseases. Traditional vaccination strategies, based on live attenuated viruses, have been ineffective at generating vaccines against these diseases, largely as result of their high toxicity. Vaccines based on protein antigens are a new vaccination strategy that have considerable promise because of their low toxicity and widespread applicability. However, the clinical success of protein-based vaccines has been limited, due to delivery problems, and new protein delivery vehicles are needed that can enhance the efficacy of protein-based vaccines.

A key limitation of current protein-based vaccines is their inability to activate cytotoxic T lymphocytes (CTL). The activation of CTL is critical for the development of immunity against viruses and tumors. CTL are activated by antigen presenting cells (APCs) through the Class I antigen presentation pathway. APCs generally only present cytoplasmic proteins as Class I antigens, although Class I antigen presentation of proteins residing in phagosomes also occurs under certain circumstances (Jondal, M., Schirmbeck, R. & Reimann, J. (1996) *Immunity* 5, 295–302.

Microparticles, 0.2–5 μm in diameter, have recently gained interest as delivery vehicles for protein-based vaccines because of their ability to enhance the Class I antigen presentation of protein antigens (Oh, Yu-Kyoung, Harding, C. V.; Swanson, J. A.; *Vaccine*. 1997, (15), 511–518; Andrianov, et al., U.S. Pat. No. 5,529,777; and Staas, et al., U.S. Pat. No. 6,321,731). Two mechanisms have been proposed to explain the ability of microparticles to enhance the Class I antigen presentation of protein antigens. The first involves disruption of phagosomes by microparticles leading to release of protein antigens into the cytoplasm of APCs, where they are processed for antigen presentation as endogenous proteins. The second uses microparticles to deliver protein antigens to phagolysosomal compartments that contain MHC I receptors That are being recycled from the plasma membrane. Once delivered these proteins are subsequently degraded by phagolysosomal enzymes into antigenic peptides that complex MHC I receptors and are then trafficked to the cell surface for antigen presentation.

Protein therapeutics have tremendous clinical potential and are currently being investigated for the treatment of cancer, vaccine development and for manipulating the host response to implanted biomaterials. However, the effective utilization of protein therapeutics requires the development of materials that can deliver bioactive material to diseased tissues and cells. At present, the majority of protein delivery vehicles are based on hydrophobic polymers, such as poly (lactide-co-glycolide) (PLGA). See O'Hagan, D. et al., in U.S. Pat. Nos. 6,306,405 and 6,086,901, and in *Adv. Drug Delivery Rev*, 32, 225 (1998). However, PLGA based delivery vehicles have been problematic because of their poor water solubility. Proteins are encapsulated into PLGA based materials through an emulsion procedure that exposes them to organic solvents, high shear stress and/or ultrasonic cavitation. This procedure frequently causes protein denaturation and inactivation as shown by Xing D et al., *Vaccine*, 14, 205–213 (1996). Hydrogels and microgels have therefore been proposed as an alternative protein delivery vehicle because they can encapsulate the protein in a totally aqueous environment, under mild conditions. See Park, K. et al., *Biodegradable Hydrogels for Drug Delivery*; Technomic Publishing Co, Lancaster, Pa. (1993); Peppas. N. A. Hydrogels in Medicine and Pharmacy; CRC press: Vol II, Boca Raton, Fla., 1986; and Lee, K. Y. et al., *Chemical Reviews*, 101, 1869-179 (2001).

A key problem in the field of hydrogel research is the development of materials that can release their contents in response to pathological stimuli, allowing for the targeting of protein therapeutics to diseased tissues and cells. A particularly important pathological stimulus is mildly acidic pH. For example, tumors exist at acidic pHs between 6.4–6.8, and the phagolysosomes of phagocytic cells are at pHs between 4.5–5.0. The acidic nature of these compartments has stimulated a need for the development of hydrogels and microgels that can selectively release their contents under mildly acidic conditions.

A particularly important application of protein delivery systems is the development of particulate materials that can deliver proteins to phagocytic cells, such as antigen presenting cells. Micron sized protein loaded hydrogels (microgels) have been investigated for this purpose because they are small enough to be phagocytosed. At present, micron sized hydrogels have been synthesized using crosslinkers that do not degrade under biological conditions, and hence have had limited success in drug delivery applications.

Currently, hydrogels are synthesized using crosslinkers that contain either, amide, ester, or carbonate linkages. Sawhney, A. et al., *Macromolecules*, 26, 581–587 (1993), describe bioerodible hydrogels based on photopolymerized poly(ethyleneglycol)-co-poly(α-hydroxy acid) diacrylate macromers which utilize an ester linkage. Sheppard, R. C. et al., in U.S. Pat. No. 5,191,015, describe an insoluble polymer with contiguous cleavable crosslinkers and functional groups, wherein the crosslinking agent is an acid degradable ketal crosslinker. Sanxia. L, et al., describe release behavior of high molecular weight solutes from poly(ethylene glycol)-based degradable networks in *Macromolecules*, 33, 2509–2515 (2000). See also Dijk-Wolthius, W. N. E. et al., *Macromolecules*. 30, 4639–4645 (1997). A crosslinked network of poly-methylmethacrylate has been synthesized using an ethylene glycol di(1-methacryloyoxy)ethyl ether crosslinker that is breakable and pH-responsive, described by Ruckenstein E. et al., *Macromolecules*. 32, 3979–3983 (1999). But networks synthesized with this crosslinker only degrade under strong acidic conditions, such as pH 2.0 and below. The hydrolysis of this type of linkage is not acid catalyzed at mildly acidic levels present in biological applications. Thus, there is a need for hydrogels and microgels that degrade under mildly acidic conditions.

BRIEF SUMMARY OF THE INVENTION

The present invention is directed to microgels for application in the delivery of proteins, vaccines, drugs (such as the anticancer drugs cisplatin, paclitaxel or taxitere), and other bioactive materials. The microgels comprise crosslinked polymer hydrogels of microparticle size, that contain or incorporate bioactive materials. The hydrogel compositions are made using an inverse microemulsion technique (aqueous droplets in an oil or aliphatic phase) that results in microgels of a predetermined size, typically 0.1–10 microns in diameter. A size range between 200 nm and 500 nm is optimal for phagocytosis by immune cells.

The microgels of the current invention release their contents in response to the mild acidic conditions found in lysosomes, tumors, inflammatory tissues and the phagolysosomes of antigen presenting cells. The present crosslinkers will hydrolyze at a preferred pH range of 4.5 to 6.8, more preferably pH 5 to 6. Prefereably, they will completely hydrolyze within 24 hours at pH 5. The current invention also specifically describes hydrogels and microgels synthesized with a bisacryloyl acetal crosslinker that hydrolyzes under acidic conditions, such as in the phagolysosome, and releases the encapsulated contents of the hydrogel or microgel after entering a cell.

The present invention provides a method of preparing a microgel composition for delivering a bioactive material to a cell, comprising the steps of (a) preparing a mixture which contains the bioactive material, a polymerizable group (i.e. the monomer to be polymerized), and a crosslinking group in an inverse emulsion where the aqueous phase contains the polymerizable group and the cross linking agent, and the aliphatic phase contains the bioactive material; (b) sonicating the mixture to achieve a pre-determined particle size, generally 0.1 to 100 microns, as determined by the time of sonication; (c) polymerizing the polymerizable group and the crosslinker in the presence of the bioactive material; and (d) recovering the resulting microgel preparation having bioactive material bound inside. Polymerization is carried out according to known reaction parameters, i.e. with a known initiator (such as potassium peroxodisulfate), and an optional catalyst such as TEMED. Alternatively the microgels are prepared and the bioactive material can be adsorbed onto the surface of the microgels, or reacted to the surface of the microgels.

The present invention thus provides an acid hydrolyzable microgel composition for delivering a bioactive molecule, comprising: an acid hydrolyzable microgel composition for delivering a bioactive molecule, comprising: a polymer backbone, which may be acrylic, dextran or other crosslinkable polymer, linked by a crosslinker; the crosslinker having the formula $R^2CH(OR^1)_2$, wherein $R^1$ is a crosslinkable, acid hydrolyzable linkage selected from one of compounds (a)–(f) of FIG. 2, $R^2$ is Ar—X where X is a water solubilizing group selected from hydrogen, methoxy, —O—$(CH_2$—$CH_2$—$O)_n$—$CH_3$ wherein n is from 1 to 10, —O—$CH_2$—$CH_2$—O—C(O)—O—Ph—$NO_2$ and —O—$CH_2$—$CH_2$—$CH_2$—NH—CO-(dextran polysaccharide), said dextran polysaccharide having a molecular weight from 300 to 100,000 daltons, preferably 300–10,000 daltons; and Ar is a homocyclic aromatic radical, whether or not fused, having 6 to 12 carbon atoms optionally substituted with one to three substituents; a particle size between 0.1–10 microns and cross linkages between 1 and 20 mole percent, sufficient to physically trap the bioactive molecule within the microgel. In accordance with convention, "Ph" represents phenyl.

In cases where dextran is used, dextran may serve as a water solubilizing group (part of the cross linker) and the polymer backbone itself. In these cases, the crosslinker of the formula $R^2CH(OR^1)_2$ containing dextran is reacted with itself in the presence of a radical source (and the bioactive material) to form the microgel composition. In this case, R is Ar—X where X is an alkyl dextran, wherein said dextran has a molecular weight from 300 to 100,000 daltons, preferably 300–10,000 daltons and an alkyl group links the aryl group to the linked dextran. In this embodiment, the $R^1$ groups crosslink to other $R^1$ groups. In contradistinction, in the acrylic polymer embodiments, the crosslinker acts through side groups (e.g. carboxyl) on the polymer backbone formed by the polymerizing units. The particle prepared as described above will have cross linkages between 1 and 20 mole percent, based on the ratio of cross linker added. This degree of crosslinking is sufficient to physically trap the bioactive molecule within the microgel.

Where dextran is used, the present synthetic strategy involves the preparation of an "activated dextran," (e.g. compound 838 in FIG. 8B and compound 914 in FIG. 9B) which is attached to a crosslinker precursor through the $R^1$ group as represented in FIG. 2. The "activated dextran" has a fraction of the glucose moieties (approximately one in six) modified at the 4 ring position to carry a reactive group such as an amine group or a nitrate group for coupling to the crosslinker precursor R group.

The above compositions preferably contain a bioactive material which is selected from the group consisting of consisting of polysaccharides, proteins, DNA and RNA. The DNA may be unmethylated (e.g. bacterial plasmid) DNA, which evokes an immune response in mammals. The biological material may also be a protein or other chemical antigen that is delivered to the lysosome of an immune cell for antigen presentation. This provides an effective vaccine.

The composition may also be designed so that $R^1$ is (a) or (b) in FIG. 2 and $R^2$ is such that Ar is phenyl and X is methoxy. This composition may further comprise a bisacryloyl acetal crosslinker for use in crosslinking acrylic polymers. A bisacryloyl acetal crosslinker will have the formula: $R^2CH(OR^1)_2$, wherein $R^1$ is selected from one of compound (a)–(d) of FIG. 2 and $R^2$ is Ar—X where X is —O—$(CH_2$—$CH_2$—$O)_n$—$CH_3$ wherein n is from 1 to 10, and aryl is a homocyclic aromatic radical, whether or not fused, having 6 to 12 carbon atoms optionally substituted with one to three substituents.

The present invention also comprises methods of preparing the compounds described herein. The methods may be particularly adapted to the synthesis of the triglyme or tetraglyme crosslinkers shown in FIGS. 6 and 7 respectively. These methods comprise the steps of (a) preparing a 1-chloro oxyalkane according to the desired n; (b) reacting the compound of step (a) with with hydroxybenzaldehyde to produce an oxyalkane-benzaldehyde; (c) converting the compound of step (c) to an acetyl with a 2,2,2-trifluoracetamide; and (d) cleaving said 2,2,2-trifluoro groups and reacting the intermediate with acryloyl chloride.

BRIEF DESCRIPTION OF THE DRAWINGS

FIG. 2 is a table showing various compositions for the present cross linkers using the generic formula $R^2$—CH(—$OR^1)_2$.

FIG. 8 is a schematic showing the synthesis of a bisacrylamide nitrochloroformate acetal crosslinker 836 and dextran microgels.

FIG. 9 is a schematic showing the synthesis of bisacrylamide dextran acetal crosslinker 920 and dextran microgels. FIG. 9D shows synthesis of dextran microgels using crosslinker 920.

DESCRIPTION OF THE PREFFERRED EMBODIMENT

Definitions

The term "hydrogel" herein refers to a three dimensional macromolecular network in water that is formed from a cross-linked polymer.

The terms "microgel", "microgel particles" and "microparticle" herein refers to a three-dimensional hydrogel particle that is 0.1–10 µm in diameter.

The term "bioactive particle" herein refers to a composition having a physiological effect in a cell, particularly a protein antigen, DNA, and enzyme or other organic molecule.

The term "acetal" herein refers to a diether in which both ether oxygens are bound to the same carbon.

The term "acryl" or "acryloyl" herein refers to the general structure (CH$_2$=CH—CO—).

The term "bisacryloyl acetal" herein is used to refer to an acetal with two acryl groups, one on each end of the acetal linkage, having the general structure of $R^2CH(—OR^1)_2$, wherein $R^1$ terminates in the structure C(O)CH=CH$_2$, as shown in FIGS. 2(a), (b), (c), and (d).

The term "crosslinker" herein refers to a molecule with two or more functional groups that can form a three-dimensional network when reacted with the appropriate co-monomers.

The term "polymerizable group" herein refers to monomers which polymerize upon introduction of an initiator or radical source.

The term "aryl" herein refers to a homocyclic aromatic radical, whether or not fused, having 6 to 12 carbon atoms optionally substituted with one to three substituents, wherein said substituents are preferably N or S.

The term "inverse emulsion" herein refers to an emulsion having an aqueous phase and an oil phase, wherein the continuous phase is the oil phase and the water-soluble droplets are dispersed in a continuous phase of oil.

The term "acrylic polymer" herein refers to a polymer made from polymerizing units (monomers) that yield a polymer having a cross linkable side chain, represented as follows:

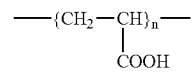

wherein said monomers are acrylic acid, acrylamide, or various monomers and mixtures thereof having hydrogen substitutions such as NH$_2$ at the CH group.

The term "loading efficiency" herein refers to the percentage of the starting amount of bioactive material that is encapsulated per milligram of the microgels (µg material/mg microgel) on average, based on the starting bioactive material/monomers ratio.

The term "alkyl-dextran" herein refers to a dextran polymer having a glycosidic linkage from a dextran through an alkyl spacer group wherein C is less than 100 and optionally substituted with amide bonds and polyethylene glycol (—O—(CH$_2$—CH$_2$—O)$_n$— where n is less than 10.

The term "lower alkane" herein refers to an aliphatic linear or branched chain or cyclic compound of the formula $C_n$—H$_{2n+2}$, where n is between 2 and 20, such as hexane, octane, nonane or the like.

The term "mole percent" herein refers, when used in connection with degree of crosslinking, that degree of cross linking as measured by the moles of crosslinker divided by the total moles of crosslinker and polymerizable groups.

Introduction

Figure 1:
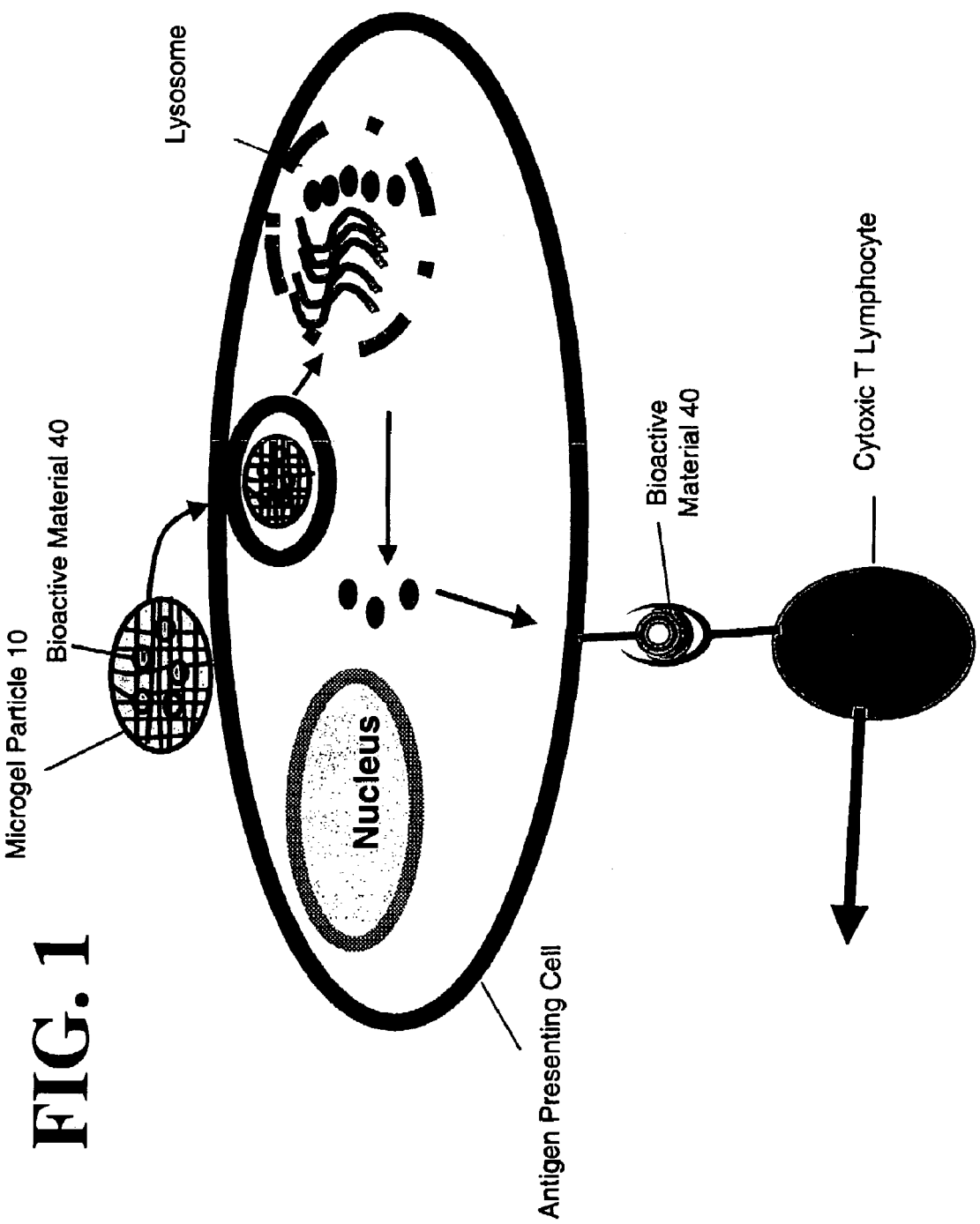
FIG. 1 is a schematic diagram showing the application of the gel materials in microparticle form being applied to an antigen presenting cell.

FIG. 1 shows a schematic diagram illustrating the overall composition and use of the present microgels. The microgels 10 of the current invention are loaded with bioactive material 40 including but not limited to, antigens, proteins, polynucleotides, polypeptides, and other bioactive material 50. The microgels 10 of the current invention should be synthesized with polymerizable groups 30 and a bisacryloyl acetal crosslinker 20 that hydrolyzes under acidic conditions and releases the encapsulated contents 40 in response to mildly acidic conditions. The mild acidic conditions found in the body such as in tumors, inflammatory tissues and in cellular compartments such as lysosomes and phagolysosomes 50 of antigen presenting cells 60 should cause the acetal group of the bisacryloyl acetal crosslinker 20 to be hydrolysed thereby degrading the microgel and releasing its contents.

In a preferred embodiment, the microgels are delivered to antigen presenting cells and then phagocytosed and trafficked to the lysosome or phagolysosome of the cells. The mild acidic conditions found in lysosomes and phagolysosomes of APCs should cause the acetal group of the bisacryloyl acetal crosslinker to be hydrolysed thereby degrading the microgels. This acid hydrolysis of the bisacryloyl acetal crosslinker increases the pore size of the microgels allowing the entrapped bioactive material to diffuse out. This swelling of the microgels increases the osmotic pressure inside the cellular compartment which causes the cellular compartment to burst, thus releasing the bioactive material into the cytoplasm where it is exposed to the MHCI protein. The MHCI protein should then display the bioactive material on the cell surface of the antigen presenting cell and activate cytotoxic T lymphocytes (CTL) which can then recognize virus, infected cells that display the bioactive material, thus targeting $CD^{+}8$ immune response.

A. The Bisacryloyl Acetal Crosslinker

1. Designing the Crosslinker

In a general embodiment, the bisacryloyl acetal crosslinker of the invention is stable to basic conditions but hydrolyzes rapidly in acidic environments. Referring now to FIG. 2, a generic formula for the bisacryloyl acetal crosslinker (labeled as Compound I) is a general structure of $R^2CH(—OR^1)_2$, where $R^1$ contains an acryl polymerizing group, and $R^2$ is a water solubilizing group. Acid degradable microgels can then be synthesized by copolymerizing this crosslinker with polymerizable groups in the presence of a bioactive material.

In general, the design of the bisacryloyl acetal crosslinker also reflects such factors as ease of synthesis, solubility, commercially available reagents, the type of hydrogel or microgel particle desired, the loading efficiency, dispersion of the particles, toxicity and the hydrolysis rates of the acetal linkage.

2. Appropriate Acryloyl Groups ($R^1$)

A key factor in choosing acryloyl groups is the chosen synthesis strategy of the crosslinker. Appropriate acryloyl groups (or acryl polymerizing group) that can be used for the bisacryloyl acetal crosslinker of this invention include but are not limited to, ethylacrylamides (a), methylacrylamides (b), acrylates (c), acrylamides (d), trifluoro-, tribromo-, trichloro- and triiodo-acetamides (e) and ethylamines (f). In a preferred embodiment, the acryloyl group ($R^1$) is an acrylamide, a substituted acrylamide, such as a methyl or ethyl acrylamide, acrylates or acrolein groups, substituted amides, and substituted vinyl groups.

3. Acid Degradable Linkages and Water Solubilizing Groups ($R^2$)

The present crosslinkers that are stable at higher than pH 7.0 but hydrolyze at a pH preferably about 5. The bisacryloyl acetal crosslinker should have an aqueous solubility of greater than 50 mg/ml. This solubility is important to insure that the microgels will be polymerizable under inverse microemulsion conditions.

Appropriate water solubilizing groups to use for $R^2$ to create the acetal linkage are compounds that contain polar groups and/or good leaving groups. Water solubilizing groups include but are not limited to, an, aryl, alkylaryl, alkoxy, aroxy or diaryl group, benzaldehyde or methoxybenzaldehyde.

The acid degradable crosslinker of the invention has advantages over other types of linkages in the prior art. In contrast, the crosslinker of the invention disclosed herein hydrolyzes on the timescale in which endosomes mature into lysosomes, in contrast to the extremely slow hydrolysis rates of cyclic ketals.

4. Water Solubilizing Groups ($R^2$) with Functional Groups

In a preferred embodiment, the crosslinker in this invention uses an aromatic acetal as the acid degradable linkage. The aromatic acetal has two important advantages over ketals, (i) their hydrolysis rates can be controlled by adding substituent water solubilizing groups in their para position, and (ii) the aromatic portion of the acetal can also act as a functional group for conjugation to biodegradable polymerizable groups, such as dextrans.

Referring now to FIG. 5A, in a preferred embodiment, an autocatalytic bisacryloyl acetal crosslinker can be used to design novel types of microgels in which an amplification of the rate of release of bioactive material is provided by each cleavage step. A strategy for using an autocatalytic bisacryloyl acetal crosslinker involves the condensation of one molecule of a carbonyl compound, such as a benzaldehyde, with two molecules of a carboxylic acid or derivative thereof. For example, FIG. 5A shows an bisacrylic benzaldehyde acetal crosslinker 530 obtained by incorporation of two acrylic acid moieties in an acetal like structure with benzaldehyde.

As shown in FIG. 5B, hydrolysis of the autocatalytic crosslinker 530 under mild acidic conditions proceeds with release of two molecules of acrylic acid. Such release contributes to increase the acidity of the medium, thereby accelerating further hydrolysis. Amplification is desirable as it may contribute to faster release of the encapsulated bioactive material possibly enabling release from the normally less acidic endosomes or other compartments of cells. Preparation of microgels using such an autocatalytic crosslinker can also be carried out using inverse emulsion polymerization with suitable co-monomers including but not limited to, hydroxymethyl methacrylate or acrylamide.

In a more preferred embodiment, $R^2$ of the bisacryloyl acetal crosslinker is a benzaldehyde acetal with a para water solubilizing group to ensure that microgels made with the crosslinker hydrolyze rapidly after experiencing the pH 5.0 environment of acidic cellular compartments. The bisacryloyl acetal crosslinker becomes acid degradable because it has two ethers connected to the same carbon. The para water solubilizing group is electron donating and causes rapid hydrolysis. The water solubilizing groups can be positioned in the ortho- and meta-positions of the benzaldehyde, however, the ease of synthesis and availability of suitable starting reagents may make these crosslinkers more difficult to synthesize.

In preferred embodiments, water solubilizing groups include but are not limited to, an alkoxy, aroxy or diaryl group, benzaldehyde or methoxybenzaldehyde, having an ortho or para functional group such as triethylene glycol (triglyme), tetraethylene glycol (tetraglyme), polyethylene glycol, nitrophenylcarbonate, dextrans, saccharides, sugars, and other carbohydrates, and combinations thereof. The size of the functional group should preferably have a molecular weight of less than 100,000. Linker groups including such groups as $(—O—CH_2—CH_2—NH—C(O)—)$ or $(—O—CH_2—CH_2—O—C(O)—O—)$ may be used to link these functional groups to the benzaldehyde acetal and aid in the addition and synthesis of these crosslinkers.

In specific embodiments, the bisacryloyl acetal crosslinker has a benzaldehyde acetal with a para functional group selected from the group consisting of: hydrogen, aldehyde, dimethyl amine, methoxy, triethylene glycol, tetraethylene glycol, polyethylene glycol, and nitrophenylcarbonate.

5. Hydrolysis of the Crosslinker for Hydrogels and Microgels

The bisacryloyl acetal crosslinker can be hydrolyzed to release the contents entrapped in the microgels of the invention in a pH dependent manner. In the preferred embodiment the bisacryloyl acetal crosslinker should preferably have a half-life at pH 5.0 of 5 minutes to 24 hours at 37° C., but a longer half life at pH 7.4 of at least 24 hours to 250 days.

In some embodiments, it may be useful for the crosslinker to have a half-life at pH 5.0, 37° C. of about 24 hours, and a half-life at pH 7.4, 37° C. of about 250 days, in order to facilitate slow release of bioactive materials. In other embodiments, it is contemplated that the half-life of the crosslinker at pH 5.0, 37° C. preferably be 5–30 minutes, and even more preferably be less than 5 minutes and a half-life at pH 7.4, 37° C. of about 24 hours in order to quickly release the bioactive materials.

The acceleration of the hydrolysis kinetics of a bisacryloyl acetal crosslinker from pH 7.4 to pH 5.0 is expected because the hydrolysis of the acetal is proportional to the hydronium ion concentration, which should increase between pH 7.4 and pH 5.0. The kinetics of acetal hydrolysis can be easily manipulated by introducing the appropriate electron withdrawing or donating groups and therefore it is possible to engineer acetal crosslinked hydrogels that have hydrolysis rates tailor-made for a given application.

The hydrolysis kinetics of the bisacryloyl acetal crosslinker changes after its incorporation into the microgels. This change in the hydrolysis kinetics of the crosslinker is potentially due to two factors, (1) the steric effects of tethering the acetal moiety of the crosslinker into the particle, which in effect generates a cyclic acetal (cyclic acetals hydrolyze 10–100 times slower than straight chain acetals because of steric reasons) and (2) the diffusion of the hydronium ion into the microgels.

A kinetic factor that may be taken into account when designing the bisacryloyl acetal crosslinker is the crosslinker's speed of hydrolysis in solution. In an embodiment where the goal is to hydrolyze the crosslinker and rapidly release the bioactive material, the bisacryloyl acetal crosslinker should preferably hydrolyze within 5–30 minutes at pH 5.0 at 37° C. This timescale is chosen because it is approximately the amount of time taken for a phagocytosed gel particle to be trafficked to cellular compartments such as lysosomes. In a preferred embodiment, these particles will degrade rapidly in the lysosome and cause lysosomal disruption. Having a particle that degrades too slowly will increase its residence time in the lysosome and allow the lysosomal enzymes increased chances of hydrolyzing the bioactive material before reaching the cytoplasm through lysosomal disruption. Therefore, in a preferred embodiment, the crosslinker should hydrolyze fairly rapidly at a preferred range of pH 7.4 to 4.5 and even more preferably between pH 6.8 to 4.5.

6. Synthesis of the Crosslinker

In a general embodiment, the bisacryloyl acetal crosslinker has the general structure of $R^2CH(\text{—}OR^1)_2$, which can be made by first synthesizing the $R^2$ water solubilizing group.

In one embodiment, the strategy for synthesis is reacting the water solubilizing group with an amino alcohol that has its amine group protected with an acid stable protecting group, such as a trifluoroacetamide, to form an acetal. The protected amines can then be deprotected and reacted with acryloyl chloride to generate the bisacrylamide acetal crosslinker. If an alcohol is used having no amino group, it can be reacted with an acryloyl chloride to make an acrylate. However, use of an acrylate may raise some solubility issues as acrylates tend to be 100-fold less soluble in the aqueous phase as acrylamides.

In a second embodiment, the strategy for synthesis involves the condensation of one molecule of the water solubilizing group with two molecules of a carboxylic acid or derivative thereof to generate an autocatalytic bisacryloyl acetal crosslinker.

Figure 4:
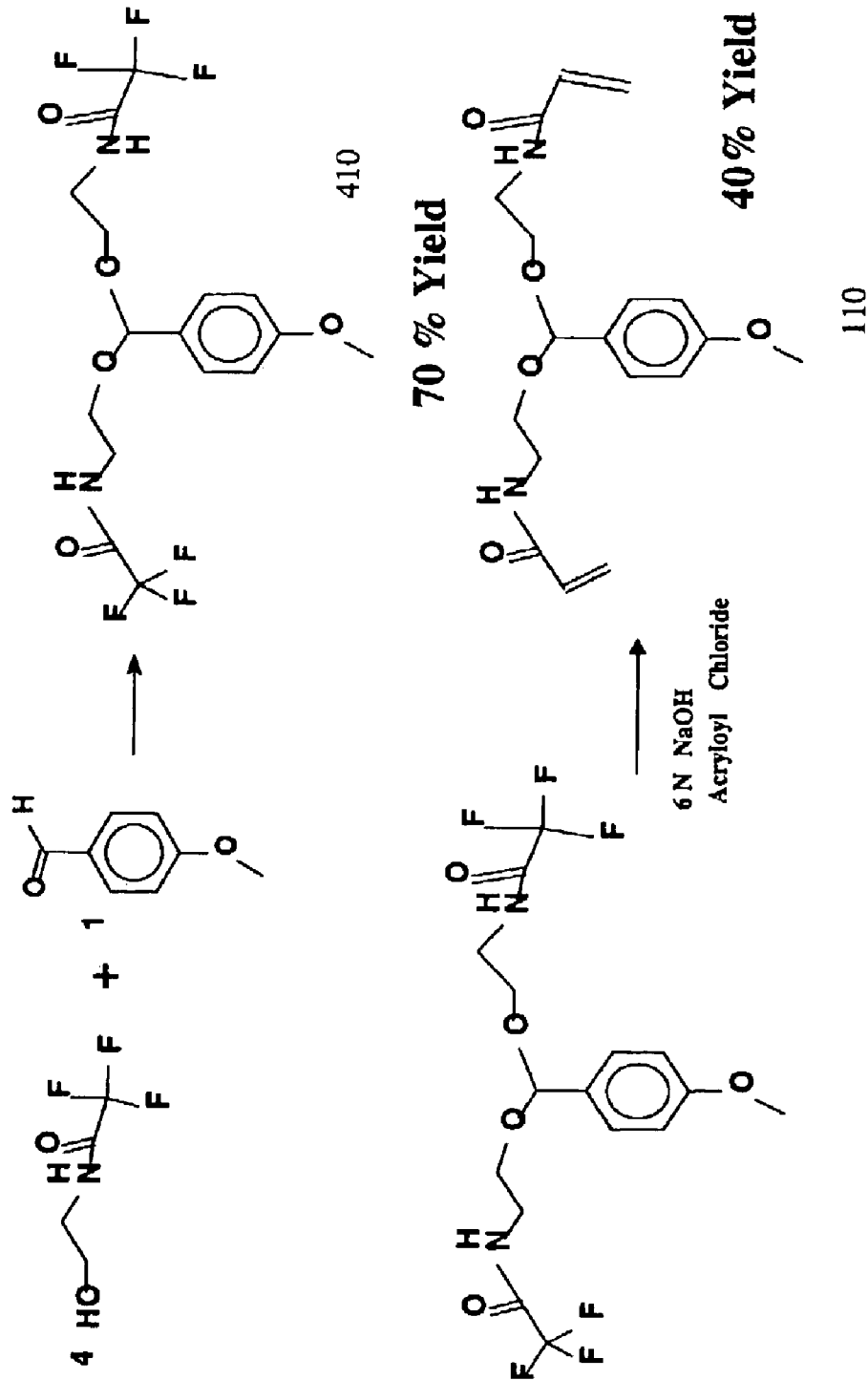
FIG. 4 is a schematic showing the synthesis of bisacrylamide methoxybenzaldehyde acetal crosslinker.
Figure 5B:
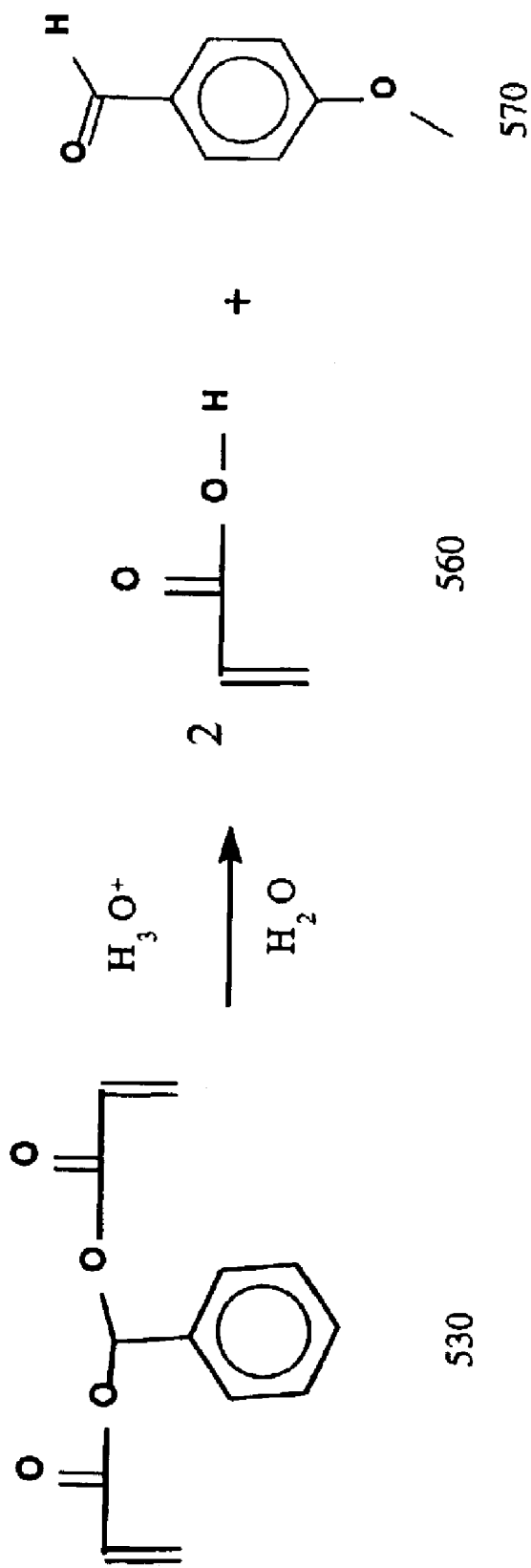
FIG. 5 is a schematic showing the synthesis of autocatalytic bisacryloyl acetal crosslinkers. Synthetic routes (5A) to these crosslinkers and their degradation under acidic conditions (5B) are shown.
Figure 6:
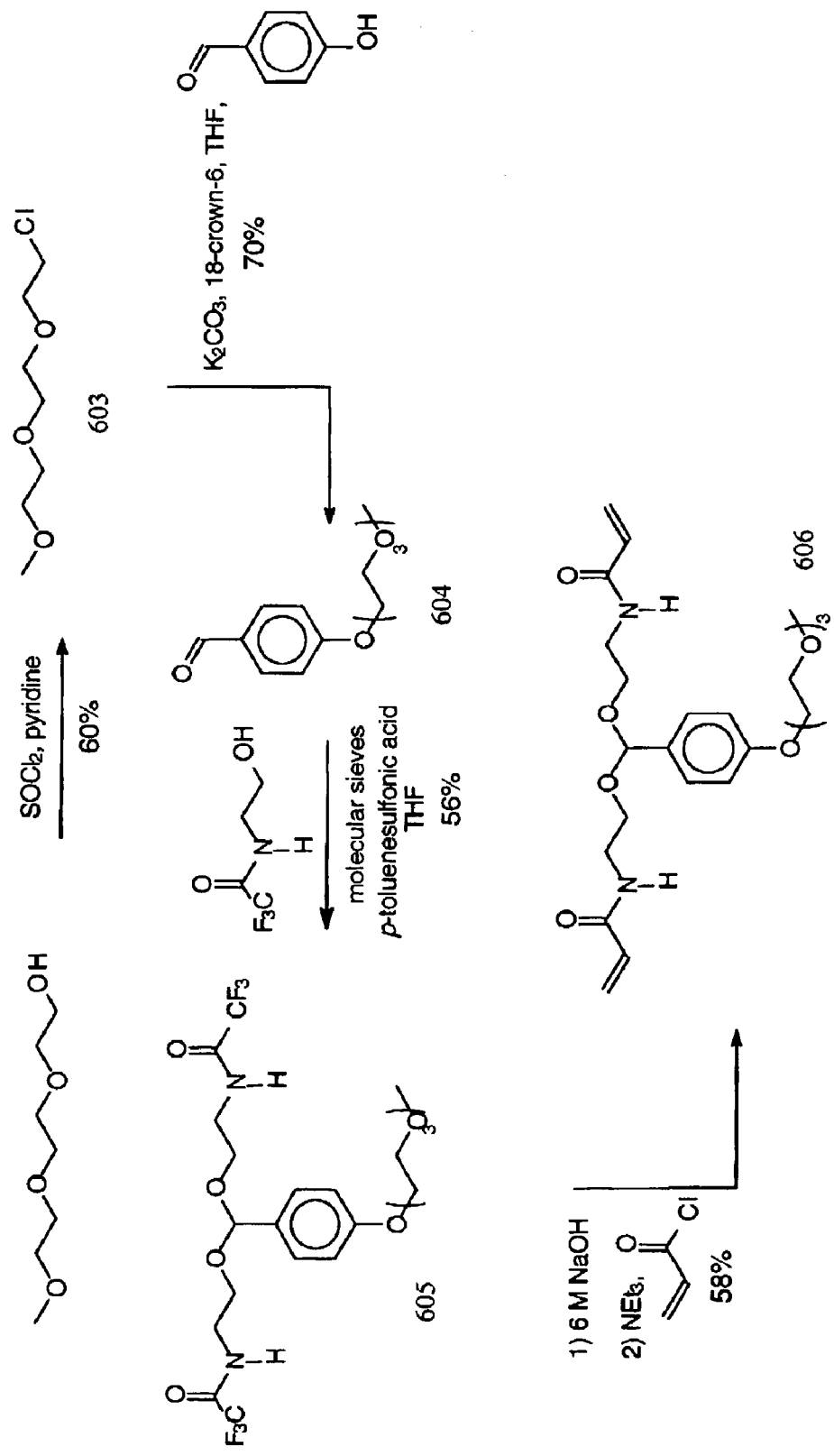
FIG. 6 is a schematic showing the synthesis of bisacrylamide triethylene glycol (triglyme) acetal crosslinker.
Figure 7:
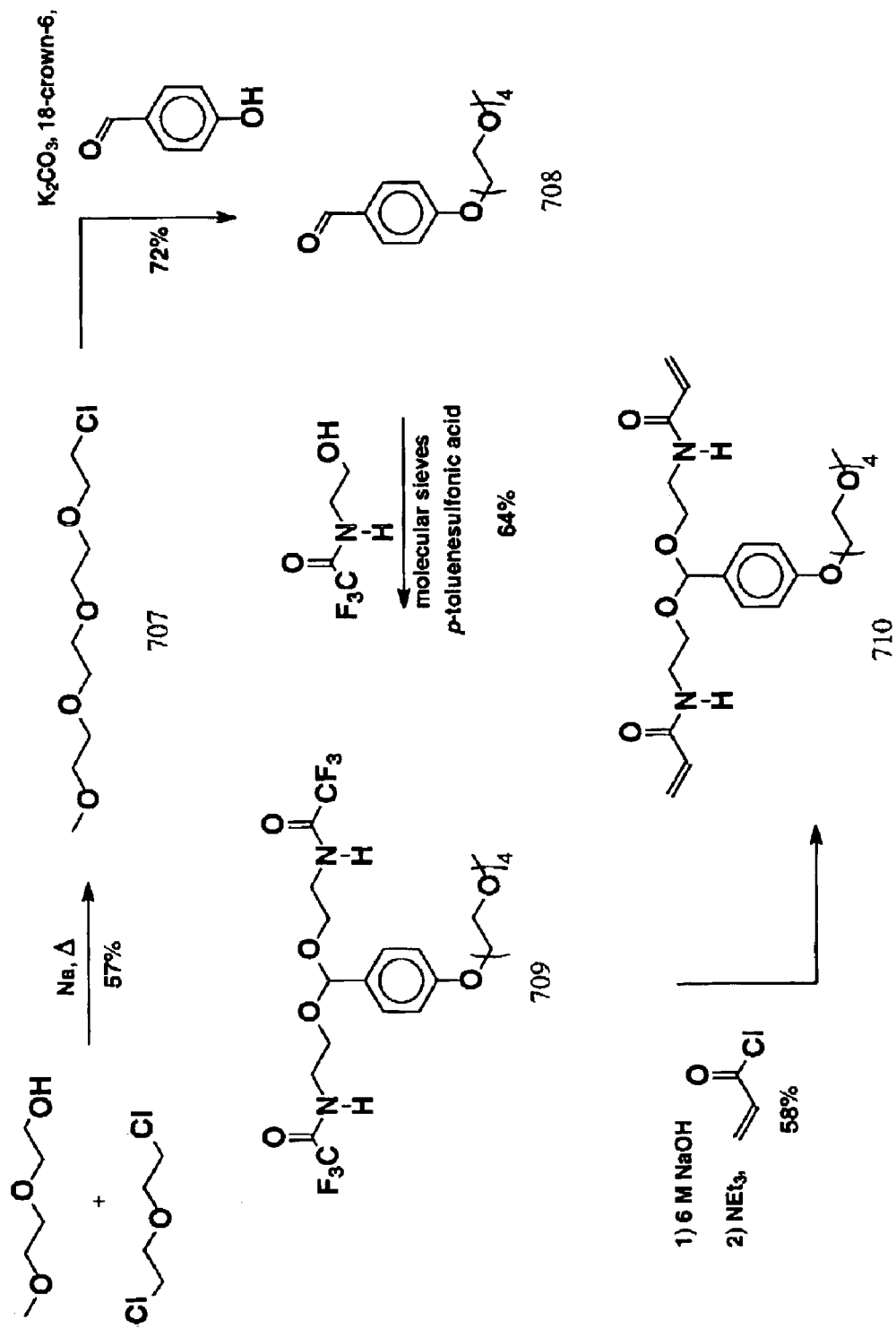
FIG. 7 is a schematic showing the synthesis of bisacrylamide tetraethylene glycol (tetraglyme) acetal crosslinker.
Figure 8A:
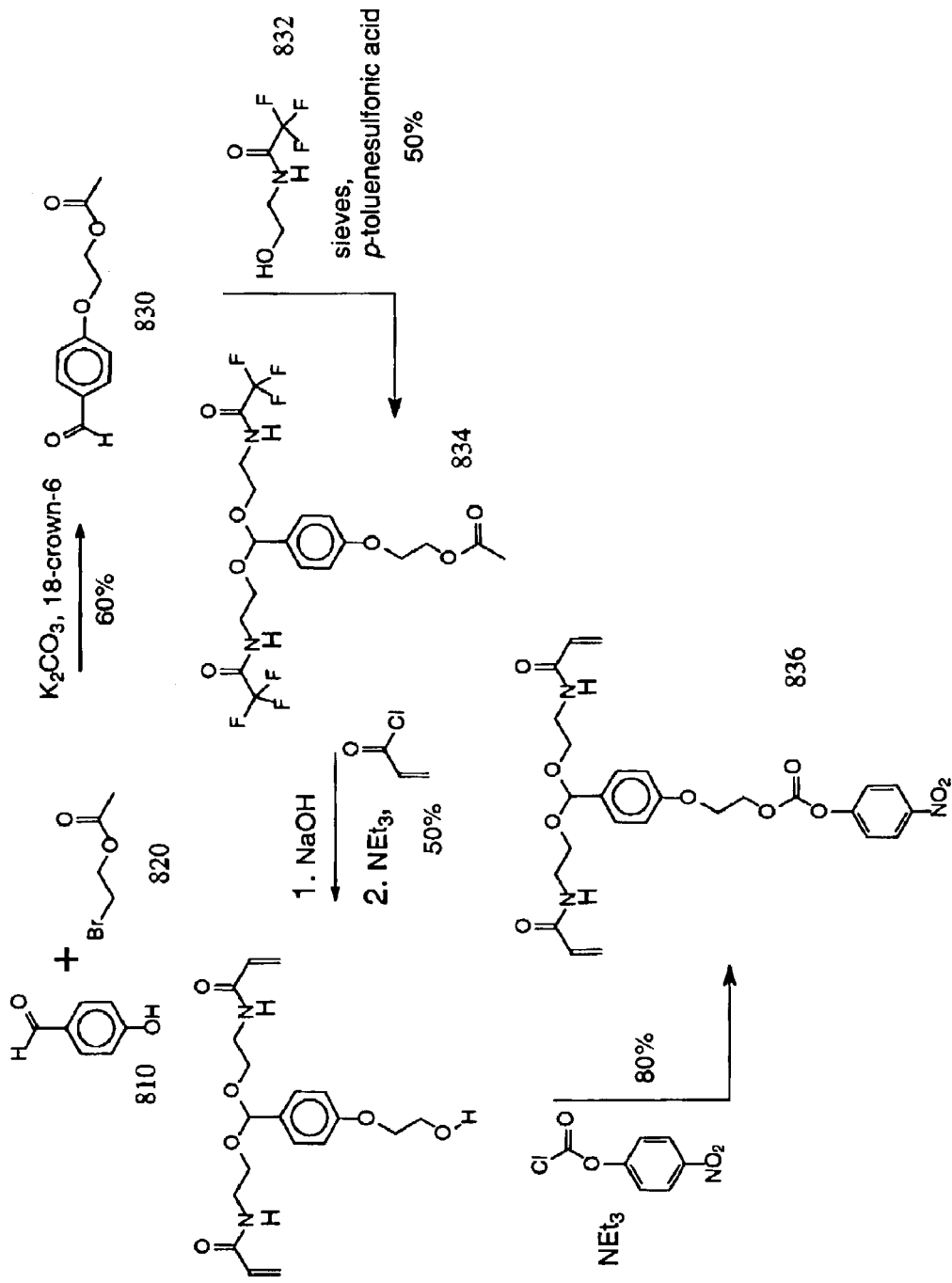
FIG. 8A shows the synthesis of the bisacrylamide nitrochloroformate acetal crosslinker 836.
Figure 9A:
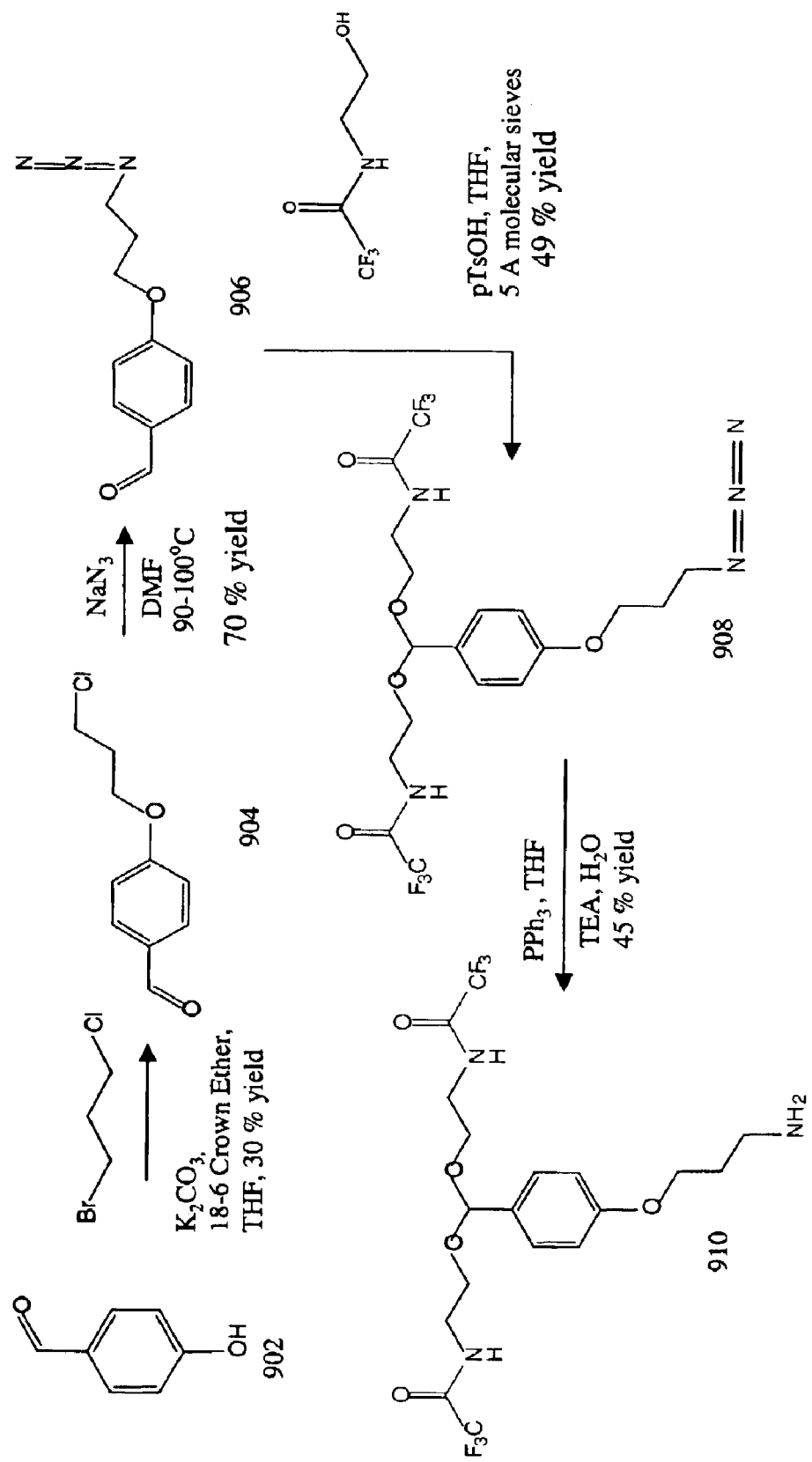
FIG. 9A shows the synthesis of the intermediate compound bisacrylamide amine acetal 910.
Figure 9B:
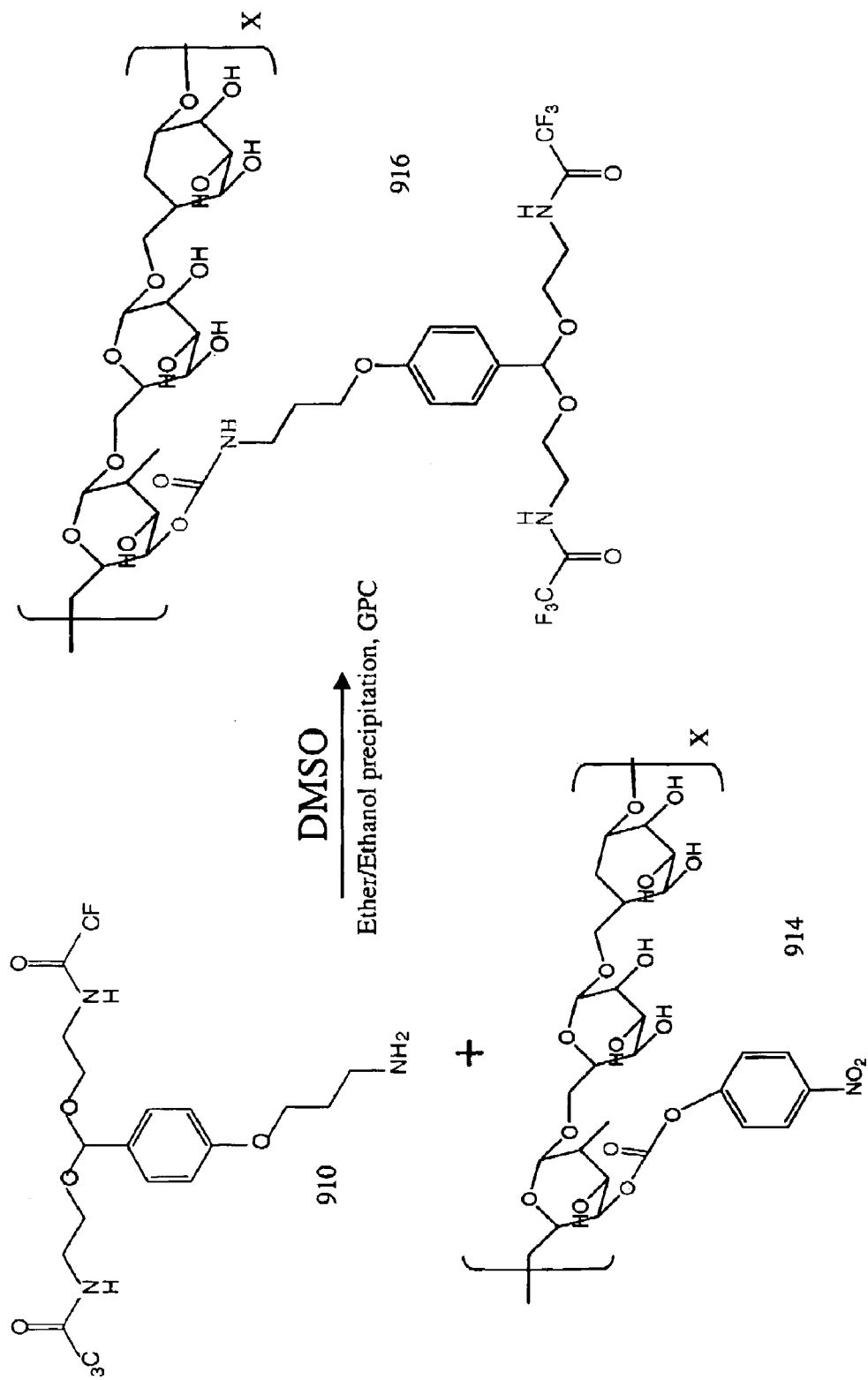
FIG. 9B shows the conjugation of the amine acetal 910 with activated dextran to yield a bistrifluoroacetamide dextran acetal 916.
Figure 9C:
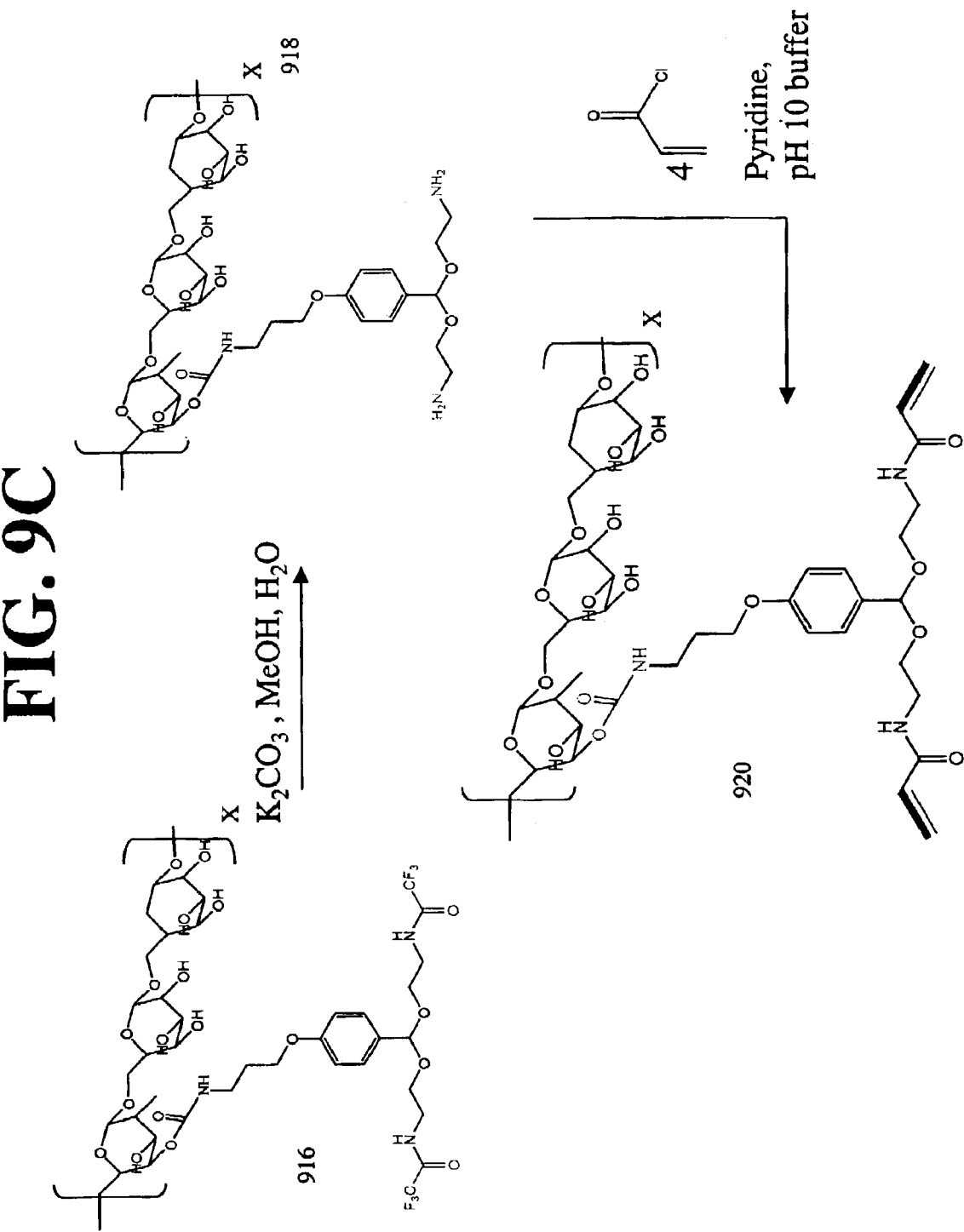
FIG. 9C shows the modification of the intermediate acetal 916 to make the bisacrylamide dextran acetal crosslinker 920.

In a preferred embodiment, the crosslinker is selected from the group consisting of: bisacrylamide methoxybenzaldehyde acetal crosslinker 110 (as shown in FIG. 4), bisacrylic benzaldehyde acetal crosslinker 530 (as shown in FIG. 5A), bisacrylamide triglyme acetal crosslinker 606 (as shown in FIG. 6), bisacrylamide tetraglyme acetal crosslinker 710 (as shown in FIG. 7), bisacrylamide nitrochloroformate acetal crosslinker 836 (as shown in FIG. 8A) and bisacrylamide dextran acetal crosslinker 920 (as shown in FIG. 9C).

Acid degradable microgels can then be synthesized by copolymerizing this bisacryloyl acetal crosslinker with polymerizable groups in the presence of a bioactive material.

B. Microgel Particles for the Delivery of Bioactive Materials

Microgels made with the bisacryloyl acetal crosslinker should efficiently entrap bioactive material with a comparable loading efficiency. In a preferred embodiment, the microgel particle size may vary between 0.1–10 μm and exhibit a loading efficiency of at least 40% bioactive material encapsulation, more preferably at least 50% loading efficiency and even more preferably at least 54% loading efficiency.

1. Appropriate Polymerizable Groups for Gel Particles

Appropriate polymerizable groups that can be used for the microgels of this invention include acrylic polymers such as, acrylamides, methacrylamides, methacrylates, and acrylates.

In more preferred embodiments, the polymerizable groups are acrylamides or methacrylamides.

Appropriate biocompatible polymerizable groups that can be used for the microgels of this invention include biocompatible polymers including but not limited to, dextrans, saccharides, mannoses, sugars, carbohydrates, nucleic acids, oligonucleotides, amino acids, polypeptides, lipids and combinations thereof.

In a more preferred embodiment, the biocompatible polymerizable group is dextrans up to 100,000 MW, more preferably up to 10,000 MW. In this embodiment, the biocompatible polymerizable group is conjugated to the functional group X of $R^2$ of the Compound I bisacryloyl acetal crosslinker before synthesis of the microgels.

2. Bioactive Materials

In a preferred embodiment, the invention contemplates entrapping such bioactive materials including but not limited to, nucleotides, polynucleotides, ribonucleotides, amino acids, peptides, proteins, antigens, plasmid DNA, growth factors and hormones, interleukins, immunostimulatory agents, drugs, vaccines, neuromodulatory agents such as neurotransmitters, stimulatory and adrenergic agents, enzymes, proteases, anticancer and antitumor agents, imaging agents, diagnostic agents, antiviral agents and antibacterial agents.

In specific preferred embodiments, the bioactive material is selected from the group consisting of: nucleotides, polynucleotides, proteins, immunostimulatory agents, vaccines, antigens, anti-viral agents, protein antigens, anticancer agents and antitumor agents.

These bioactive materials can be conjugated with a carrier molecule or they can be conjugated to a polymerizable group and copolymerized into the microgels. The linkage between the polymerizable group and the bioactive molecule can be designed to be cleaved under various physiological conditions. The bioactive material can also be adsorbed onto the surface of the microgels, or reacted to the surface of the microgels.

3. Synthesis of Microgels

In general, microgels can be synthesized by inverse microemulsion polymerization according to the procedure described by Kriwet, B.; Walter, E.; Kissel, T.; *J. Control Release*, 1998, (56), 149–158, which describes synthesis of bioadhesive poly(acrylic acid) nano- and microparticles using an inverse emulsion polymerization method for the entrapment of hydrophilic drug candidates. A key issue in the synthesis of microgels by inverse emulsion polymerization is the aqueous solubility of the acryloyl groups and polymerizable groups. The solubility of both the acryloyl groups and polymerizable groups are very important as all of the polymerizable components in an inverse emulsion polymerization must be sufficiently water soluble.

During the inverse microemulsion polymerization, a small amount of water is dispersed into an organic phase and stabilized by surfactants. Sonication before polymerization for about 5 minutes will insure the correct particle size, which will cover a range of sizes, within the range of about 100 nm–10 μm, preferably 100 nm–5 μm. The polymerizable groups and the bisacryloyl acetal crosslinker are then polymerized in the aqueous phase in the presence of the bioactive material and an initiator molecule or radical source. Since polymerization is initiated and contained within water droplets, mainly spherical crosslinked microgel particles containing entrapped bioactive material are produced. To adjust particle size, either longer sonication time or larger surfactant concentration will decrease the microgel particle size.

Several different emulsion polymerization procedures were attempted using different organic phases and surfactant blends. Inverse polymerizations with toluene/chloroform as the continous phase and pluronic F-68 as the surfactant were unsuccessful. However, inverse polymerizations with hexane as the continous phase and SPAN™ 80 (sorbitan monooleate), TWEEN™ 80 (polyethyleneglycol-sorbitan monooleate), dioctyl sulfosuccinate (AOT) and Brij 30 (Polyoxyethylene (4) Lauryl ether) (all from Sigma Aldrich, St. Louis, Mo.) as surfactants are successful in producing microgels.

That the bisacryloyl acetal crosslinker exhibits improved performance in forming microgel particles in hexane/water versus chloroform-toluene/water is potentially explained by the lower solubility of the crosslinker in hexane versus chloroform-toluene. For example, the bisacryloyl acetal crosslinker has water/hexane partition ratio of 10,000:1. In contrast, the water/toluene-chloroform partition ratio is only 1:1, suggesting that in the water/chloroform-toluene polymerizations, a large fraction of the crosslinker is lost in the organic phase. Thus, the organic phase is most preferably hexane and the surfactants used are preferably TWEEN™ 80, SPAN™ 80, dioctyl sulfo succinate (AOT) and Brij or combinations thereof. More preferably the surfactant used is a 1:3 ratio of TWEEN™ 80/SPAN™ 80. Furthermore, it is important that the surfactants used for synthesis be neutral and FDA approved for human use. Neutral, biocompatible surfactants are preferred for the synthesis of bioactive material-loaded microgel particles because of their reduced interactions with proteins and lower toxicity.

4. Loading and Loading Efficiency of Entrapped Bioactive Materials

The bisacryloyl acetal crosslinker can affect that loading efficiency and the amount of bioactive material entrapped in the microgels of the invention. Loading efficiency is the amount of bioactive material that is entrapped within the gel particles as compared to the total starting amount of bioactive material placed in the polymerization reaction. In general, the loading efficiency of the microgel particles of the invention should not appreciably change with the crosslinking ratio, however, the water solubilizing groups can change the loading and encapsulation efficiencies.

The loading efficiency is different from the amount of protein encapsulated in a single particle. It is estimated that approximately 1 million protein molecules of about 50 kD size can be encapsulated in a microgel. This number comes from assuming the microgel has a density of 1, a radius of 0.5 microns, and are composed of 10% protein by weight.

In a general embodiment, the microgel particles of the invention should have at least a 20% loading efficiency, more preferably 40% loading efficiency, even more preferably at least 50% loading efficiency, and most preferably more than 55% loading efficiency.

In a preferred embodiment, wherein the bioactive material loaded is DNA material, the loadings and efficiencies of the microgel particles should be comparable to other microparticle systems which have efficiencies purported to be about 1–2 μg DNA/mg polymer for 500 nm PLGA particles. (See Garcia del Barrio, G.; Novo, F. J.; Irache, J. M. *Journal of Controlled Release* (2003), 86(1), 123–130). It is estimated that about 3,000–7,000 molecules of DNA can be encapsulated within a single microgel of the present invention, if the DNA encapsulated was 6,000 bp, which has a MW of about 4 million daltons. The loading efficiencies for the amount of DNA material entrapped in microgel particles of the preferred embodiment should preferably be at least 40%, more preferably at least 50% and even more preferably at least 54%.

In a preferred embodiment, wherein the bioactive material loaded is protein, the loading efficiencies for the amount of protein entrapped in microgel particles of the preferred embodiment should be at least 20%, preferably at least 40%, more preferably around 50%.

The loading efficiency and the amount of bioactive material entrapped is an important aspect in light of such factors as the amount of bioactive material needed to be delivered to the target for an effective dose and the amount of available bioactive material. A major drawback in previous therapeutics and vaccines is there is often difficulty in obtaining large enough amounts of the therapeutic composition of bioactive material for production. Therefore, it is a goal of the invention to make microgels with high loading efficiencies so as to lower the starting amount of bioactive material required at the beginning of polymerization.

D. Release of Entrapped Bioactive Materials

The release of bioactive materials from the loaded gel particles made with the bisacryloyl acetal crosslinker can be first measured at various mild pHs at 37° C., in aqueous solutions. In a preferred embodiment, the crosslinker should hydrolyze within 5 minutes to 24 hours at pH 5.0 and have a much slower hydrolysis rate at pH 7.4.

In a preferred embodiment, these microgels will degrade rapidly in the lysosomes and cause lysosomal disruption. Therefore, in a preferred embodiment, at a more acidic pH 5.0, encapsulated bioactive materials should preferably be 80% released from the microgel particles within 6 hours, preferably completely released from the microgel particles within 12 hours, more preferably within 8 hours, and even more preferably within 6 hours. At pH 7.4, the release of entrapped bioactive materials 40 should be significantly slower, taking up to 150 hours for the microgel particles to completely release their contents.

The molar ratio between the concentration of polymerizable groups and the bisacryloyl acetal crosslinker affects the rate of bioactive material released from the gel particles. It is preferred that the microgels of the present invention have 1–20 mole percent crosslinking, between 1%–12.8% crosslinking, and most preferred between 1%–3% crosslinking, but sufficient to physically trap the bioactive molecule within the microgel.

For example, a molar ratio of 9:1 acrylamide/bisacryloyl triglyme-acetal crosslinker (1.6% crosslinking) results in a linear release of bioactive material, with nearly 80% released at 300 minutes. A ratio of 4:1 of acrylamide to bisacryloyl triglyme-acetal crosslinker (3.5% crosslinking) results in a steeper initial increase in release of bioactive material with a slower increase from 100–200 minutes and an second steep increase from 200–300 minutes. A small molar ratio of 1:1 acrylamide/bisacryloyl triglyme-acetal crosslinker (12.8% crosslinking) results in a very slow release of 20% of the bioactive material in the first 175 minutes and a steep release of bioactive material.

Thus, depending on the desired rate of release of bioactive material, the amount of crosslinker can be increased or decreased. In general, 1–3% crosslinking may be preferred, not only for its steady linear release of bioactive material, but also because of the crosslinker's effects upon other factors such as toxicity, loading efficiency, and amount of T-cell activation. But it is contemplated that in some embodiments, increased amounts of crosslinker may be more preferred, such as in a case for example, where the crosslinker size is small.

E. Antigen Presentation and T-cell Activation

The microgels release their bioactive material payload into the cytoplasm of cells upon lysosomal disruption. Higher loading capacity of the gel particles may also lead to greater antigen presentation of the encapsulated bioactive material.

In the antigen presentation assay described by Sanderson, S.; Shastri, N. in *Inter. Immun.* 1994, 6, 369–376, the β-galactosidase activity of B3Z T cells is measured. Antigen presenting cells display the peptide having the sequence, SINFEKL, upon phagocytosis of ovalbumin. These cells were engineered to transcribe β-galactosidase when in the presence of antigen presenting cells displaying the SINFEKL peptide. β-galactosidase then liberates chlorophenol red from the chlorophenol red βgalactoside that is present in solution. Absorbance of chlorophenol red is measured by UV absorbance at 595 nm. Therefore this assay can be used as a measurement of the amount of bioactive material delivered into the cytoplasm of cells by the microgel particles of the invention by measuring the amount of liberated chlorophenol red by UV absorbance at 595 nm.

A proper control would be to compare the amount presented by the gel particles 10 of the invention when incubated with the SINFEKL peptide which is directly displayed on the antigen presenting cells and not delivered to the cytoplasm of the cells first. A maximum absorbance of 0.25 should be observed, which results in 100% T-cell activation. In a preferred embodiment, the bioactive loading capacity and efficiency should lead to an absorbance of preferably at least 0.15, more preferably 0.2, and most preferably more than 0.25, using the antigen presentation assay described by Sanderson, S.; Shastri, N. in *Inter. Immun.* 1994, 6, 369–376.

A preferred basic minimal level of antigen presentation that the particles should effectuate is about 50% T-cell activation as the minimum level of T-cell activation. Efficient microgels should need approximately 500 micropaticles per antigen presenting cell. The level beyond which the starting amount of bioactive material and micrgels compared to the amount of antigen presentation is inefficient and unpreferred is considered about 5 mg/ml of microgels to generate a 100% T cell activation. This level is inefficient and unpreferred because of the potential toxicity involved with the delivery vehicles.

F. Toxicity of Gel Particles and Degraded Gel Particles

Use of this invention in human and mammalian therapeutics brings up issues of the toxicity of these microgels. As the amount of crosslinker and polymerizable groups increases, the viability of cells decreases. The viability of cells can be measured by the ability of mitochondria in metabolically active cells to reduce yellow tetrazolium salt (MTT) to form insoluble purpose formazan crystals.

In a preferred embodiment, the target antigen presenting cells should preferably exhibit at least 50% viability after 24 hours of incubation with the gel particles of the invention, more preferably at least 70% viability after 24 hours, even more preferably at least 80% viability and most preferably more than 90% viability after 24 hours according to the MTT assay as described above and in Example 14.

Polymers with high MW are not easily excreted from body, therefore another aspect of the invention is to make microgel particles that easily and safely excreted by the body after being degraded in the acidic cellular compartment. In general it is preferred that the microgel particles degrade into linear polymer chains are 100,000 daltons or less. Thus, dextran microgels are one preferred embodiment because dextrans degrade into chains of 10,000 daltons or less.

Another factor in the size of the degraded particles is the amount of crosslinker used. As described in Example 16, lower amounts of crosslinker used result in smaller linear polymer chains, therefore making excretion of the degraded particles more likely. However, the inability of cells to secrete larger polymer chains may not be problematic as the amount of particles to which the cells are exposed are very small. Furthermore, the toxicity studies show that cells are still viable after long-term exposure to the microgel particles.

G. Applications for Acid Degradable Hydrogels and Microgels

This strategy for the synthesis of acid degradable microgels has many applications including the delivery of bioactive materials, including but not limited to polynucleotides, polypeptides, proteins, peptides, antibodies, vaccines, antigens, genetic, or therapeutic agents, to the cytoplasm of phagocytic cells.

1. Vaccine Therapeutics

In one embodiment, the microgels of the present invention would have applications in vaccine therapeutics and disease prevention. Protein loaded microgels could be injected as an intramuscular injection to a patient, stimulating phagocytosis by macrophages and antigen presenting cells. After being sequestered in lysosomes, the acid degradable linkage of the bisacryloyl acetal crosslinker would hydrolyze, releasing the protein antigen, and cause the lysosome to swell and then burst, thereby releasing the lysosome contents into the cellular cytoplasm. Once the protein antigen is released into the cytoplasm, MHCI proteins can then bind the protein antigen and present the protein antigen on the cell membrane. These cells would then initiate the cytotoxic T lymphocyte immune response against pathogens from which the protein antigen came from.

The gel particles of the invention would be particularly useful in combating infections that need a strong cytotoxic T lymphocyte response, including diseases such as HIV/AIDS and Hepatitis C infections. Examples of such antigens which can be used as bioactive material and entrapped in the microgels of the present invention, include but are definitely not limited to, the TAT protein from HIV, the ENV protein from HIV, the Hepatitis C Core Protein from the Hepatitis C virus, the prostatic acid phosphatase for prostate cancer and the protein MART-1 for melanoma.

2. Gene Therapy

In a second embodiment, the microgels of the invention would be used for gene therapeutics. Since gene therapy involves the delivery of a sequence of DNA to the nucleus of a cell, the microgels of the invention would be especially suited for this application. Once a polynucleotide is delivered by the microgels to the cytoplasm, the polynucleotide can undergo translation into a protein. This has the potential, then, to make proteins that are not normally produced by a cell.

In a preferred embodiment, the bioactive material would be a plasmid that encodes for a protein or antigenic peptide initially. For example, one would use a plasmid that encodes for a protein that would display antigens for cancer. These proteins would not be easy to generate in multi-milligram to gram quantities to be delivered to a patient, therefore using the microgels of the present invention to deliver plasmid DNA encoding these antigens is a preferred alternative. Plasmid DNA, encapsulated in the microgels of the invention and delivered to the cytoplasm of phagocytic cells, has been shown to be active and still able to transfect cells.

In addition to encoding for a gene, plasmid DNA has the added characteristic of generating an immune response because plasmid DNA is generated from bacteria. Bacterial DNA has two major differences compared with vertebrate DNA: 1) bacterial DNA has a higher frequency of CG dinucleotides in the sequence ($\frac{1}{16}$ dinucleotides in microbial DNA are CG pairs, but only 25% of that is observed in vertebrate DNA); and 2) bacterial DNA is unmethylated as compared to vertabrate DNA which is often methylated. Vertebrate systems will recognize the plasmid DNA then as being foreign, and the cell will react as for a bacterial infection. This immune response is manifested in the production of cytokines and interleukins that then go on to activate T cells, B cells, and other cells, proteins, and cellular machinery involved in the immune response. Example 20 demonstrates that bacterial DNA delivered by microgels indeed increases the production of interleukins.

3. Directing Patient Immune Response

In a further embodiment, the plasmid DNA used as the bioactive material would have an added interleukin sequence. (Egan, Michael A.; Israel, Zimra R. *Clinical and Applied Immunology Reviews* (2002), 2(4–5), 255–287.) Interleukins are secreted peptides or proteins that mediate local interactions between white blood cells during immune response (B. Alberts et al, *Molecular Biology of the Cell*, 4th ed., Garland Science, 2002). Different interleukins (e.g. IL-12, IL-2) will direct the type of immune response that is generated. IL-6, IL-1, 8, 12, and TNF-α are secreted by infected macrophages as an immune response and IL-6 serves to activate lymphocytes and increase antibody production. The differentiation of helper T cells into either $T_H1$ or $T_H2$ efffector cells determines the nature of the response. A $T_H1$ response is characterized by a CTL response; a $T_H2$ response is characterized by antibody production.

The addition of the interleukin-2 or 12 (IL-2 or IL-12) gene sequence, and its subsequent translation into an interleukin protein may allow the direction of the type of patient immune response and amplification of the desired CTL response by adding or displaying immunostimulatory groups on the surface of the microgels. Such immunostimulatory groups include but are not limited mannose, plasmid DNA, oligonucleotides, ligands for the Toll receptors, interleukins and chemokines. T-cells activate B-cells to secrete Interleukin-6 (IL-6) to stimulate B cells into antibody-secreting cells.

It has been shown by Apostolopoulos, V.; McKenzie, I. F. C. *Current Molecular Medicine* (2001), 1(4), 469–474, that activation of the mannose receptors on the surface of APCs leads to enhanced CTL activation.

Incorporation of mannose onto the present microgels by copolymerizing a mannose polymerizable group with the polymerizable groups and the crosslinker to make microgels should likely result in increased CTL response. The synthesis of activated mannose is shown in FIG. 18.

4. Particle Carriers and Dispersion

In other embodiments, oligonucleotides (approximately 12–75 bases in length) can be used for immunostimulation as well as for their antisense activity. However, because oligonucleotides are too small to remain encapsulated inside the microgels of the invention, they must be conjugated to a polymerizable group and then later released. One way to solve this problem would be to attach the oligonucleotides to a polymerizable group through an acid degradable linkage similar to creating a second crosslinker, whereby acid hydrolysis in the acidic conditions will release the oligonucleotide.

Alternatively, the oligonucleotides can be conjugated to a large macromolecule, such as dextran through an acid degradable linkage which is then physically entrapped in the microgels.

The microgels of the invention can be suspended or stored in a conventional nontoxic vehicle, which may be solid or liquid, water, saline, or other means which is suitable for maintaining pH, encapsulation of the bioactive material for an extended period of time, sufficient dispersion or dilution of the microgels and the overall viability of the microgels for their intended use.

Preferably the microgel particles of the invention are stored in dry state (vacumm dried) and stored at 4° C. for several months. The microgels can be dispersed in buffer and sonicated or vortexed for a few minutes to resuspend into solution when needed. The microgels should be vortexed or sonicated for a sufficient amount of time to resuspend the microgels evenly in solution, however, not too long as vortexing and sonication can also damage some proteins and bioactive material. The microgel particles are ready for delivery upon visual determination that the microgels are sufficiently dispersed in solution. The solution should be opaque with no visible aggregates floating.

5. Pharmaceutically Effective Delivery and Dosages

The loaded microgels of the invention can be administered by various suitable means to a patient, including but not limited to parenterally, by intramuscular, intravenous, intraperitoneal, or subcutaneous injection, or by inhalation. The delivery of the microgels to a patient is preferably administered by injection once but does not preclude the necessity for multiple injections that would be required to illicit the desired level of immune response.

The amount of microgels needed to deliver a pharmaceutically effective dosage of the bioactive material to effect the CTL response in a patient will vary based on such factors including but not limited to, the crosslinker and polymerizing group chosen, the protein loading capacity and efficiency of the gel particles, the toxicity levels of the biodegraded particles, the amount and type of bioactive material needed to effect the desired response, the subject's species, age, weight, and condition, the disease and its severity, the mode of administration, and the like.

One skilled in the art would be able to determine the pharmaceutically effective dosage. In general, the amount of bioactive material that could be administered by the microgels of the invention is from 1 ng to more than 1 gram quantities.

The examples, methods, procedures, treatments, specific compounds and molecules contained herein are meant to exemplify and illustrate the invention and should in no way be seen as limiting the scope of the invention. Any patents or publications mentioned in this specification are indicative of levels of those skilled in the art to which the patent pertains and are hereby incorporated by reference to the same extent as if each was specifically and individually incorporated by reference.

EXAMPLE 1

Synthesis and Delivery of Microgels

Figure 3:
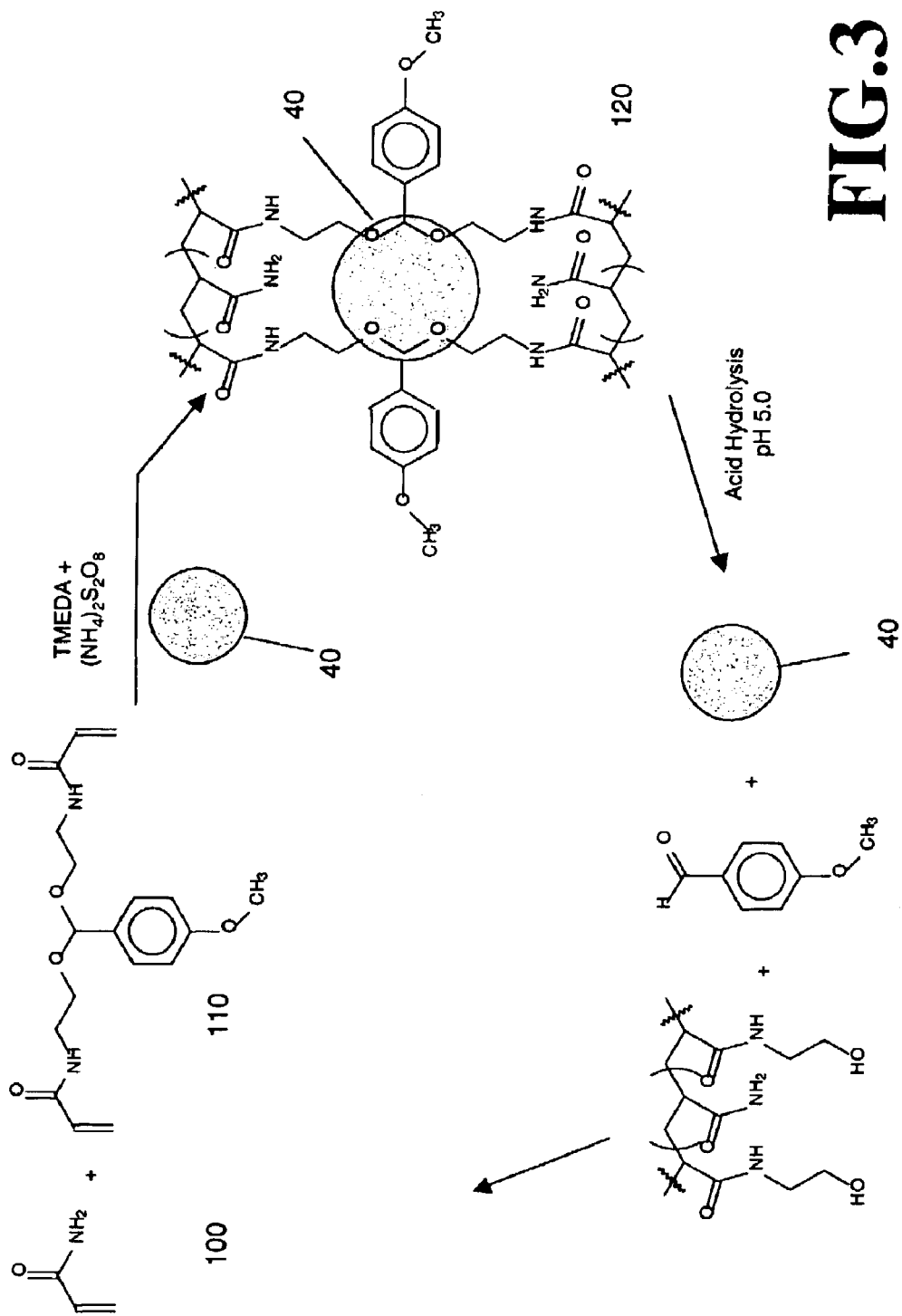
FIG. 3 is a synthetic scheme showing the manufacture of a microgel having a polymer, a cross linker, and a bioactive material, and the subsequent dissolution of the particle.

Referring now to FIG. 3, an exemplary process for the synthesis of a microgel particle for pH-dependent degradation is shown. A polymerizable acrylic group 100 is added to the bisacrylamide methoxybenzaldehyde acetal crosslinker 110 (which is described in the following example) wherein $R^1$=(a) of FIG. 2 and $R^2$=aryl-methoxy. The polymerization reaction is carried out by inverse microemulsion, initiated by an initiator such as TMEDA and diammonium persulfate and carried out in the presence of bioactive particle 40, and carried out in the presence of bioactive particle 40.

At neutral pHs, the bisacrylamide methoxybenzaldehyde acetal crosslinker 110 remains intact and the release of entrapped bioactive material 40 is significantly slower or not at all. Under acidic conditions, the acetal group hydrolyses and increases the pore size of microgels made with it, releasing the entrapped bioactive materials 40, and degraded particles, in the form of multiple polymer chains 140 and a small molecule aldehyde 130.

EXAMPLE 2

Synthesis of a Bisacrylamide Methoxy Benzaldehyde Acetal Crosslinker

Referring to FIG. 4, the bisacrylamide methoxy benzaldehyde acetal crosslinker 110 was synthesized in two steps. The first step was acetal formation with hydroxy-trifluoroacetamide and methoxy benzaldehyde using the procedure of Roelofsen et al., *Recueil*, 90, 1141–1152 (1971), which gave a 70% yield of bistrifluoroacetamide methoxy benzaldehyde acetal 410 after chromatography. In the second step, the intermediate was then deprotected with 6N NaOH and reacted with acryloyl chloride to yield the crosslinker 110 (FIG. 3) in 40% yield after chromatography. In the crosslinker 110, $R^2$ (according to the generic formula of FIG. 2) was methoxy benzaldehyde (methoxy aryl).

EXAMPLE 3

Synthesis of an Autocatalytic Bisacryloyl Acetal Crosslinker

A strategy for synthesis of an autocatalytic bisacryloyl acetal crosslinker involves the condensation of one molecule of carbonyl compound such as a benzaldehyde with two molecules of a carboxylic acid or derivative thereof. In this case, $R^1$=(c) of FIG. 2, and $R^2$=aryl-H.

FIG. 5A shows a bisacrylic benzaldehyde acetal crosslinker 530 obtained by incorporation of two acrylic acid moieties in an acetal like structure with benzaldehyde. Referring now to FIG. 5A, para methoxy benzaldehyde 510 is reacted with acrylic anhydride 520 in the presence of sulfuric acid to form the autocatalytic bisacrylic benzaldehyde acetal crosslinker 530. Also shown is an alternative synthesis is to react dibromo-toluene with sodium acrylate 550 to form the crosslinker 530.

In addition to the same acid degradable linkage, hydrolysis of the autocatalytic crosslinker under mild acidic conditions proceeds with release of two molecules of acrylic acid. Such release contributes to increase the acidity of the medium, thereby accelerating further hydrolysis. This autocatalytic crosslinker can be used to design microgels which rely on a hydrolysis reaction as shown in FIG. 5B in which an amplification of the rate of release is provided by each cleavage step. Such amplification is desirable as it may contribute to faster release of the encapsulated bioactive material possibly enabling release from the normally less acidic endosomes compartments of cells. Referring now to FIG. 5B, the cross linker 530 of the present example will yield, upon hydrolysis, 2 molecules of acrylic acid 560 and p-methoxy benzaldehyde 540.

Preparation of microgel particles using this release-amplified crosslinker can also be carried out using inverse emulsion polymerization with suitable co-monomers such as hydroxymethyl methacrylate or acrylamide.

EXAMPLE 4

Synthesis of Bisacrylamide Triethylene Glycol Acetal Crosslinker

Referring now to FIG. 6, a more hydrophilic acid degradable crosslinker, containing a hydrophilic triethylene glycol (triglyme) moiety is shown. Since the crosslinker of Example 2 is relatively hydrophobic, it was hypothesized that decreasing its hydrophobicity would improve its performance since inverse emulsion polymerizations are very sensitive to the hydrophobic/hydrophilic balance of the reactants. This modification dramatically increased the hydrophilicity of the crosslinker making it compatible with a variety of inverse emulsion polymerization procedures.

The bisacrylamide triethylene glycol acetal crosslinker (606) or triglyme crosslinker as shown in FIG. 6 was synthesized in four steps on a multigram scale. The first step involved the preparation of 1-chloro-3,6,9-trioxadecane (603) using the procedure of Loth, H. & Ulrich, F. (1998) *J. Control Release*. 54, 273. Compound 603 was then used to alkylate hydroxy benzaldehyde (605) and produce p-(1,4,7, 10-Tetraoxaundecyl)benzaldehyde (604). Compound 603 was chosen as the alkylating agent since it can be easily synthesized on a large scale (100 grams) enabling the preparation of 4 on a 20 gram scale (70% yield), using potassium carbonate as the base and 18-crown-6 as the phase transfer catalyst. Hydroxy-benzaldehyde could also be alkylated using 1-tosyl-3,6,9-trioxadecane and 1-bromo-3,6,9-trioxadecane but these approaches were discontinued because significantly lower yields of the desired product were obtained.

Compound 604 was converted to an acetal (605) by reaction with N-(2-hydroxyethyl)-2,2,2-trifluoroacetamide. A potential problem with acetal formations is the separation of the product from residual alcohol. The alcohol is generally used in 4–6 fold molar excess over the aldehyde, and even high yielding reactions leave 2–4 molar equivalents of the alcohol to be removed. Initial attempts at purifying the acetal product 605 from unreacted N-(2-hydroxyethyl)-2,2,2-trifluoroacetamide using flash chromatography were unsuccessful. However, 605 could be purified by crystallization from ethyl acetate/hexane, allowing for its synthesis on a multigram scale. The final bisacrylamide triethylene glycol acetal crosslinker was obtained by cleaving the trifluoroacetyl groups on 605 in 6 M NaOH/Dioxane followed by reaction of the resulting diamine with an excess of acryloyl chloride. Final purification of the corsslinker was achieved by crystallization from ethyl acetate/hexane.

1-Chloro-3,6,9-trioxadecane (603). Spectroscopic data agreed with those reported in the literature. $^{13}$C NMR (CDCl$_3$): δ 42.16, 58.30, 69.92, 69.96, 69.98, 70.70, 71.30. Anal. Calcd. for C$_7$H$_{15}$O$_3$Cl: C, 46.03; H, 8.28. Found: C, 45.68; H, 8.39, yield 70%.

p-(1,4,7,10-Tetraoxaundecyl)benzaldehyde (604). Chloride 603 (26 g, 0.14 mol, 1.3 equiv) and p-hydroxybenzaldehyde (13 g, 0.11 mol, 1 equiv) were dissolved in dry THF (40 mL). K$_2$CO$_3$ (15 g, 0.11 mol, 1 equiv) was added followed by 18-crown-6 (3.0 g, 11 mmol, 0.11 equiv) and KI (0.20 g, 1.2 mmol, 0.01 equiv). The reaction mixture was stirred at reflux for 48 h. The resulting mixture was cooled to room temperature, and water (200 mL) was added. The product was extracted with 3×350 mL portions of ethyl acetate and the combined organic layers were dried and concentrated. The oil was loaded onto a silica gel column and eluted with a 1:9 mixture of ethyl acetate/hexane, followed by a ratio of 1:4, 3:7, 4:1 of ethyl acetate/hexane and finally washed with ethyl acetate to afford 21 g (70%) of 604 as a clear oil. IR (cm$^{-1}$): 1697 (s), 1165 (s). $^1$H NMR (400, CDCl$_3$): δ 3.36 (s, 3), 3.54 (t, 2, J=4.6), 3.63–3.68 (m, 4), 3.72–3.75 (m, 2), 3.88 (t, 2, J=4.8), 4.20 (t, 2, J=4.8), 7.01 (d, 2, J=8.8), 9.87 (s, 1). $^{13}$C NMR (CDCl$_3$): δ 58.86, 67.59, 69.29, 70.40, 70.47, 70.71, 71.73, 114.71, 129.84, 13.1.76, 163.69, 190.63. Calcd: [M+H]$^+$ (C$_{14}$H$_{21}$O$_5$) m/z=269.13889. Found FAB-HRMS: [M+H]$^+$ m/z=269.134487. Anal. Calcd. for C$_{14}$H$_{20}$O$_5$: C, 62.67; H, 7.51. Found: C, 62.47; H, 7.74.

N,N'-Bistrifluoroacetyl-di-(2-aminoethoxy)-[4-(1,4,7,10-tetraoxaundecyl)phenyl]methane (605). Aldehyde 604 (3.60 g, 13.4 mmol, 1 equiv) and N-(2-hydroxyethyl)-2,2,2-trifluoroacetamide (15.0 g, 95.5 mmol, 7.1 equiv) were dissolved in dry THF (50 mL). p-Toluenesulfonic acid (0.360 g, 2.09 mmol, 0.16 equiv) and 5 Å molecular sieves (50 g) were added. The reaction mixture was stirred overnight and was quenched with triethylamine (10 mL, 72 mmol, 5.3 equiv). The reaction mixture was filtered to remove the molecular sieves with a buchner funnel. A 150 mL portion of water was added to the filtrate and was then extracted with four 150 mL portions of ethyl acetate. The ethyl acetate was evaporated and the product was recrystallized twice from ethyl acetate/hexane, recovering 4.03 grams of 605 (60%). MP: 90.2–91.3° C. IR (cm$^{-1}$): 3280 (br), 1702 (s), 1562 (m), 1210 (s), 1180 (s). $^1$H NMR (400 MHz, DMSO-d$_6$): δ 3.22 (s, 3), 3.37–3.42 (m, 6), 3.49–3.57 (m, 10), 3.72 (t, 2, J=4.6), 4.07 (t, 2, J=4.6), 5.52 (s, 1), 6.91 (d, 2, J=8.7), 7.29 (d, 2, J=8.7), 9.51 (t, 2, J=5.5). $^{13}$C NMR (DMSO-d$_6$): δ 39.22, 58.00, 62.57, 67.12, 68.91, 69.59, 69.78, 69.93, 71.26, 100.57, 113.93, 116.14 (q, J=241), 127.72, 130.26, 156.40 (q, J=36), 158.52. Calcd: [M]$^+$ (C$_{22}$H$_{30}$F$_6$N$_2$O$_8$) m/z=564.1906. Found FAB-HRMS: [M]$^+$ m/z=564.1922. Anal. Calcd. for C$_{22}$H$_{30}$F$_6$N$_2$O$_8$: C, 46.81; H, 5.36; N, 4.96. Found: C, 46.97; H, 5.38; N, 4.72.

N,N'-Bisacryloyl-di-(2-aminoethoxy)-[4-(1,4,7,10-tetraoxaundecyl)phenyl]methane (606). Compound 605 (4.0 g, 7.1 mmol, 1 equiv) and 6 M NaOH (30 mL) were added to dioxane (20 mL) and the reaction mixture was stirred at room temperature for 7 h. Complete removal of the acetamide groups was determined by TLC using ninhydrin staining. Upon completion, the reaction mixture was cooled to 0° C. and triethylamine (3 mL) was added. Acryloyl chloride (12 mL, 0.15 mol, 21 equiv) and triethylamine (36 mL, 0.26 mol, 36 equiv) were added in small alternating portions while periodically monitoring the pH to maintain it above 7. A 10% K$_2$CO$_3$ in water solution (30 mL) was added, and the reaction mixture was stirred for 10 minutes before extracting the product with four 200 mL portions of ethyl acetate. The organic layers were combined, dried, and evaporated and the product crystallized from ethyl acetate/hexane, yielding 2.05 g (58%) of the crosslinker as a white solid. MP: 83.6–85.5° C. IR (cm$^{-1}$): 3293 (br), 1665 (s), 1562 (s), 1245 (s), 1101 (s). $^1$H NMR (400 MHz, CDCl$_3$): δ 3.38 (s, 3), 3.53–3.76 (m, 16), 3.86 (t, 2, J=4.8), 4.14 (t, 2, J=4.8), 5.44 (s, 1), 5.65 (dd, 2J=17, J=2), 6.15 (dd, 2, J=17, J=10), 6.22 (s, 2), 6.30 (dd, 2, J=10, J=2), 6.91 (d, 2J=8.8), 7.32 (d, 2, J=8.8). $^{13}$C NMR (DMSO-d$_6$): δ 38.71, 58.04, 63.80, 67.10, 68.93, 69.61, 69.80, 69.94, 71.27, 100.83, 113.91, 125.10, 127.86, 130.62, 131.69, 158.45, 164.72. Calcd: [M+H]$^+$ (C$_{24}$H$_{37}$N$_2$O$_8$) m/z=481.2549. Found FAB-HRMS: [M+H]$^+$ m/z=481.2544. Anal. Calcd. for C$_{24}$H$_{36}$N$_2$O$_8$: C, 59.99; H, 7.55; N, 5.83. Found: C, 59.86; H, 7.75; N, 5.77.

EXAMPLE 5

Synthesis of Bisacrylamide Tetraglyme Acetal Crosslinker

FIG. 7 shows the synthetic pathway of another crosslinker, in which R$^1$=(a) of FIG. 2 and R$^2$=aryl-O-[CH$_2$—CH$_2$—O]$_4$—CH$_3$, referred to as "tetraglyme." This crosslinker has properties, as compared to the other crosslinkers disclosed herein, including, but not limited to, increased protein loading and loading efficiency, better dispersability in solution, and higher T-cell activation achieved.

1-Chloro-3,6,9,12-tetraoxatridecane (707). This compound was prepared according to the procedure reported by Schafheute et al. [16] IR (cm$^{-1}$): 2875 (s), 1149 (s). $^1$H NMR (300 MHz, CDCl$_3$): δ 3.38 (s, 3), 3.55 (t, 2, J=4.6), 3.75 (t, 2, J=5.9), 3.60–3.67 (m, 12). $^{13}$C NMR (CDCl$_3$): δ 42.36, 58.60, 70.11, 70.19, 70.21, 70.24, 70.96, 71.55. Calcd: [M+H]$^+$ (C$_9$H$_{20}$O$_4$Cl) m/z=227.1050. Found FABHR-MS: [M+H]$^+$ m/z=227.1045. Anal. Calcd. for C$_9$H$_{19}$O$_4$: C, 47.68; H, 8.45. Found: C, 47.83; H, 8.62.

p-(1,4,7,10,13-Pentaoxatetradecyl)benzaldehyde (708). Chloride 707 (4.85 g, 21.45 mmol, 2 equiv.) and p-hydroxybenzaldehyde (1.31 g, 10.72 mmol, 1 equiv) were dissolved in dry THF (5 mL). K$_2$CO$_3$ (1.49 g, 10.75 mmol, 1 equiv.) was added followed by 18-crown-6 (50 mg, 0.19 mmol, 0.01 equiv.) and KI (50 mg, 0.301 mmol, 0.01 equiv.). The reaction mixture was stirred and heated at reflux for 24 hours. The reaction mixture was cooled down to room temperature and water (50 mL) was added. The product was extracted with ethyl acetate (3×50 mL) and the combined organic layers were dried and evaporated. The oil was loaded onto a silica gel column and eluted with a 1:1 ethyl acetate/hexane mixture to afford 2.41 g (72%) of 704 as a clear oil. IR (cm$^{-1}$): 1693 (s), 11.32 (s). $^1$H NMR (300 MHz, CDCl$_3$): δ 3.33 (s, 3), 3.50 (t, 2, J=4.5), 3.72–3.58 (m, 10), 3.86 (t, 2, J=4.8), 4.18 (t, 2, J=4.8), 6.99 (d, 2, J=8.7), 7.79 (d, 2, J=8.6), 9.80 (s, 1). $^{13}$C NMR (CDCl$_3$): δ 58.82, 67.59, 69.26, 70.32, 70.41, 70.43, 71.73, 114.70, 129.84, 131.74, 163.68, 190.59. Calcd: [M+H]$^+$ (C$_{16}$H$_{25}$O$_6$) m/z=313.1651. Found FABHR-MS: [M+H]$^+$ m/z=313.1643.

p-(1,4,7,10,13-Pentaoxatetradecyl)benzylacetal-bistrifluoroacetamide (709). Aldehyde 708 (0.88 g, 2.8 mmol, 1 equiv.) and N-(2-hydroxyethyl)-2,2,2-trifluoroacetamide (4.02 g, 21.3 mmol, 7.6 equiv.) were dissolved in dry THF (6 mL). p-Toluenesulfonic acid (95 mg, 0.5 mmol, 0.16 equiv.) and 5 Å molecular sieves (7 g) were added. The reaction mixture was stirred overnight and was quenched with triethylamine (0.5 mL, 3.6 mmol, 1.3 equiv.). The reaction mixture was filtered. Water (50 mL) was added. The product was extracted into ethyl acetate (5×50 mL) and the solvent was evaporated. In order to remove the excess alcohol, benzoyl chloride (1.82 mL, 31.4 mmol, 1 equiv.), triethylamine (4.37 mL, 62.8 mmol, 2 equiv.), and dry THF (10 mL) were added. The reaction mixture was stirred at room temperature for 1 hour. Water (100 mL) was added and the product was extracted into ethyl acetate (5×100 mL) and the solvent was evaporated. The remaining oil was loaded onto a silica gel column and eluted with a 3:7 ethyl acetate/hexane mixture followed by a 4:1 ethyl acetate/hexane mixture to afford 1.11 g (64%) of 709 as a white solid. MP: 74.6–75.0° C. IR (cm$^{-1}$): 3292 (br), 1701 (s), 1560 (m), 1209 (s), 1178 (s). $^1$H NMR (400 MHz, DMSO-d$_6$): δ 3.21 (s, 3), 3.34–3.41 (m, 6), 3.46–3.58 (m, 14), 3.72 (t, 2, J=4.6), 4.07(t, 2, J=4.6), 5.52 (s, 1), 6.91 (d, 2, J=8.4), 7.29 (d, 2, J=8.4), 9.53 (t, 2, J=5.6). $^{13}$C NMR (DMSO-d$_6$): δ 39.22, 58.01, 62.56, 67.12, 68.89, 69.56, 69.76, 69.81, 69.91, 71.26, 100.54, 113.92, 115.19 (q, J=288), 127.72, 130.25, 156.38 (q, J=36), 158.51. Calcd: [M+H]$^+$ (C$_{24}$H$_{34}$F$_6$N$_2$O$_9$) m/z=608.2168. Found FABHR-MS: [M]$^+$m/z=608.2153. Anal. Calcd. for C$_{24}$H$_{34}$F$_6$N$_2$O$_9$: C, 47.37; H, 5.63; N, 4.60. Found: C, 47.20; H, 5.84; N, 4.54.

p-(1,4,7,10,13-Pentaoxatetradecyl)benzylacetal-bisacrylamide (710). Compound 709 (400 mg, 0.66 mmol, 1 equiv.) and 6M NaOH (2.8 mL) were added to dioxane (1.8 mL) and the reaction mixture was stirred at room temperature for 3.5 hours. Complete removal of the acetamide groups was monitored by TLC and ninhydrin staining. Upon completion, the reaction mixture was cooled down to 0° C. and triethylamine (0.6 mL) was added. Acryloyl chloride (1.1 mL, 13.8 mmol, 21 equiv.) and triethylamine (5.6 mL, 40.4 mmol, 61 equiv.) were added in small alternating amounts while periodically monitoring the pH so that it did not go below 7. A 10% K$_2$CO$_3$ in water solution (40 mL) was added and the reaction was stirred for 10 minutes before extracting the product into ethyl acetate (6×40 mL). The organic layers were dried and evaporated to afford a yellow oil. The oil was loaded onto a silica gel column and eluted with a 2:1 ethyl acetate/hexane mixture followed by ethyl acetate and a 1:9 methanol/ethyl acetate mixture to afford 200 mg (58%) of 710 as a white solid. MP: 62.0–63.0° C. IR (cm$^{-1}$): 3302 (br), 1657 (s), 1541 (m), 1102 (s). $^1$H NMR (300 MHz, DMSO-d$_6$): δ 3.21 (s, 3), 3.29 (t, 2, J= 4.5), 3.39–3.55 (m, 18), 3.72 (t, 2, J=4.6), 4.07 (t, 2, J=4.6), 5.49 (s, 1), 5.56 (dd, 2, J=10, J=2), 6.10 (dd, 2, J=17, J=2), 6.30 (dd, 2, J=17, J=10), 6.90 (d, 2, J=8.6), 7.32 (d, 2, J=8.6), 8.20 (t, 2, J=5.5). $^{13}$C NMR (DMSO-d$_6$): δ 38.67, 58.01, 63.77, 67.07, 68.88, 69.54, 69.74, 69.78, 69.89, 71.24, 100.80, 113.88, 125.06, 127.83, 130.60, 131.67, 131.87, 158.42, 164.68. Calcd: [M+Li]$^+$ (C$_{26}$H$_{40}$N$_2$O$_9$Li) m/z=531.2893. Found FABHR-MS: [M+Li]$^+$ m/z=5.31.2883. Anal. Calcd. for C$_{26}$H$_{40}$N$_2$O$_9$: C, 59.53; H, 7.69; N, 5.34. Found: C, 59.19; H, 7.63; N, 5.04.

EXAMPLE 6

Hydrolysis Kinetics of a Bisacryloyl Acetal Crosslinker

A key aspect of the bisacryloyl acetal crosslinker is its hydrolysis kinetics. The crosslinker is designed to be stable at the physiological pH of 7.4 but it undergoes rapid hydrolysis at acidic pHs. This is demonstrated by measurements performed with the bisacrylamide methoxybenzaldehyde acetal crosslinker 110 at pH 5.0 and at pH 7.4. At pH 5.0, the crosslinker hydrolyzes rapidly, with a half-life of 5.5 minutes, whereas at pH 7.4 the half-life is 24 hours.

A stock solution of the bisacrylamide methoxybenzaldehyde acetal crosslinker (10 mg/mL) in THF was prepared and 10.5 μL (1×10$^{-4}$ mol/L) was added to a 3.0 ml PBS solution at either pH 5.0 or 7.4, in a spectrophotometer cuvette. The hydrolysis of the acetal was monitored by measuring the absorbance of the 4-methoxybenzaldehyde, produced by the acetal hydrolysis, at 280 nm. The percentage of hydrolysis was calculated by the following equation: percent hydrolysis (%) at time i=(A$_i$–A$_0$)/(A$_\infty$–A$_0$)×100%, where A=Absorbance at 280 nm. At pH 5.0, 95% hydrolysis was complete in 20 minutes, with about 50% hydrolysis in less than 10 minutes.

The acceleration of the hydrolysis kinetics of this crosslinker from pH 7.4 to pH 5.0 was apparent. The hydrolysis of such benzaldehyde acetals is proportional to the hydronium ion concentration, which increases 250 fold between pH 7.4 and pH 5.0. The second order hydrolysis rate constant of a bisacrylamide methoxybenzaldehyde acetal crosslinker is 5,610 min$^{-1}$mole$^{-1}$. The hydrolysis rate constant of this crosslinker is 5 times slower than the hydrolysis rate constant of the dimethyl acetal of methoxy benzaldehyde. This rate reduction of the bisacrylamide methoxybenzaldehyde acetal crosslinker may be due to the electron withdrawing effects of the amide groups on the alkoxy portion of the acetal and is beneficial because it increases shelf life.

EXAMPLE 7

Synthesis of Acid Degradable Microgel Particles Encapsulating Bioactive Material Using Inverse Microemulsion Technique Microgel particles were synthesized by inverse microemulsion polymerization, according to the procedure described by Kriwet, B.; Walter, E.; Kissel, T.; *J. Control Release*, 1998, (56), 149–158. A key issue in the synthesis of microgels by inverse emulsion polymerization is the aqueous solubility of the monomers. Several different emulsion polymerization procedures were attempted with the bisacrylamide acetal crosslinker, using different organic phases and surfactant blends. Inverse polymerizations with toluene/chloroform as the continous phase and pluronic F-68 as the surfactant were unsuccessful. However, inverse polymerization with hexane as the continous phase and of SPAN™ 80

(sorbitan monooleate), TWEEN™ 80 (polyethyleneglycol-sorbitan monooleate, AOT and Brij as surfactants were successful in producing microgels.

The improved performance of the bisacrylamide methoxy benzaldehyde acetal crosslinker 110 in hexane water versus chloroform-toluene/water is potentially explained by the lower solubility of the crosslinker in hexane versus chloroform-toluene. For example, the bisacrylamide methoxy benzaldehyde acetal crosslinker 110 has water/hexane partition ratio of 10,000:1, in contrast the water/toluene-chloroform partition ratio is only 1:1, suggesting that in the water/chloroform-toluene polymerization a large fraction of the crosslinker is lost in the organic phase.

The following protocol illustrates the preparation of the present microgel particles encapsulating a bioactive material (albumin). These particles are discussed further in connection with Example 11. Table 1 of Example 11 sets forth the components of three different microgel particles. In this example, microgel particles with crosslinking ratios ranging from 1.6%–12.8% were prepared using this inverse emulsion polymerization procedure with bisacrylamide triglyme acetal crosslinker 606 of Example 4 and acrylamide.

The organic phase of the polymerization consisted of 5 mL of hexane containing 150 mg of a 3:1 weight ratio of SPAN™ 80 and TWEEN™ 80. The aqueous phase of the polymerization consisted of 125, 200, or 225 mg of acrylamide and 25, 50 or 125 mg of the bisacrylamide triglyme acetal crosslinker of Example 4 (with a combined weight of 250 mg), dissolved in 0.5 ml of sodium phosphate buffer pH 8.0 300 mM sodium phosphate, 12 mg of the free radical initiator potassium peroxodisulfate and 5.4 or 5.7 mg ovalbumin. The aqueous and organic phases were deoxygenated with nitrogen. An inverse emulsion between the organic and aqueous phases was formed by mixing them and then sonicating for 30 seconds. Polymerization of the inverse emulsion was then initiated while stirring with a magnetic bar by adding 10 μl of N,N,N',N'-tetramethylethylene diamine. The stirred polymerization was allowed to proceed for 10 minutes at room temperature.

After polymerization, the mixture was centrifuged at 2800 rpm for 10 minutes and the solvent was decanted off. The microgels were carefully washed with hexane (2×20 mL), acetone (4×20 mL) and isolated by centrifugation at 2,800 rpm for 10 minutes. The recovered microgels were vacuum dried overnight and analyzed by scanning electron microscopy (WDX ISI-ds130C, Microspec Corp.) at 15 kV. A scanning electron microscopy (SEM) image of the particles (not shown) showed that the particle size varied between 200 nm and 500 nm in the dry state. This size distribution is suitable for protein delivery to APCs, which internalize particles between 200 nm–5 μm by phagocytosis.

EXAMPLE 8

Synthesis of Bisacrylamide Nitrophenylcarbonate Acetal Crosslinker

The goal of synthesizing microgel particles with dextran was to generate microgel particles that would degrade to a low molecular weight excretable backbone. Referring now to FIG. 8, a bisacrylamide nitrophenylcarbonate acetal crosslinker 836 can be synthesized by the synthesis steps as shown in FIG. 8A.

The synthesis of the bisacrylamide nitrophenylcarbonate acetal crosslinker 836 was accomplished in four steps. The first step was alkylation of hydroxy benzaldehyde 810 with bromo-ethylacetate 820, using potassium carbonate and 18-6 crown as the base. The product was purified by a small silica gel column, and this synthesis could be performed on a 20 gram scale. The second step was acetal formation between hydroxy-ethyl trifluoroacetamide 830 and the benzaldehyde acetate 830 from previous, using p-toluene sulfonic acid as a catalyst. The product, bistrifluoroacetamide methoxyphenyl-ethyl acetate 834 (50% yield), was purified by crystallization from ethyl acetate and hexane, using 5 A molecular sieves and could be synthesized on a multigram scale. The bistrifluoroacetamide methoxyphenyl-ethyl acetate 834 was then deprotected in 6N NaOH and reacted with acryloyl chloride, the reaction product was purified by crystallization from ethyl acetate, to give the hydroxyl compound 835. This reaction needs to be performed in 6N NaOH otherwise the hydroxyl will react with the acryloyl chloride. The compound 835 was converted to the bisacrylamide nitrophenylcarbonate acetal crosslinker 836 by reacting with para-nitrochloroformate, in the presence of triethyl amine. The crosslinker 836 was purified by crystallization from ethyl acetate.

EXAMPLE 9

Synthesis of Dextran Microgels

Figure 8B:
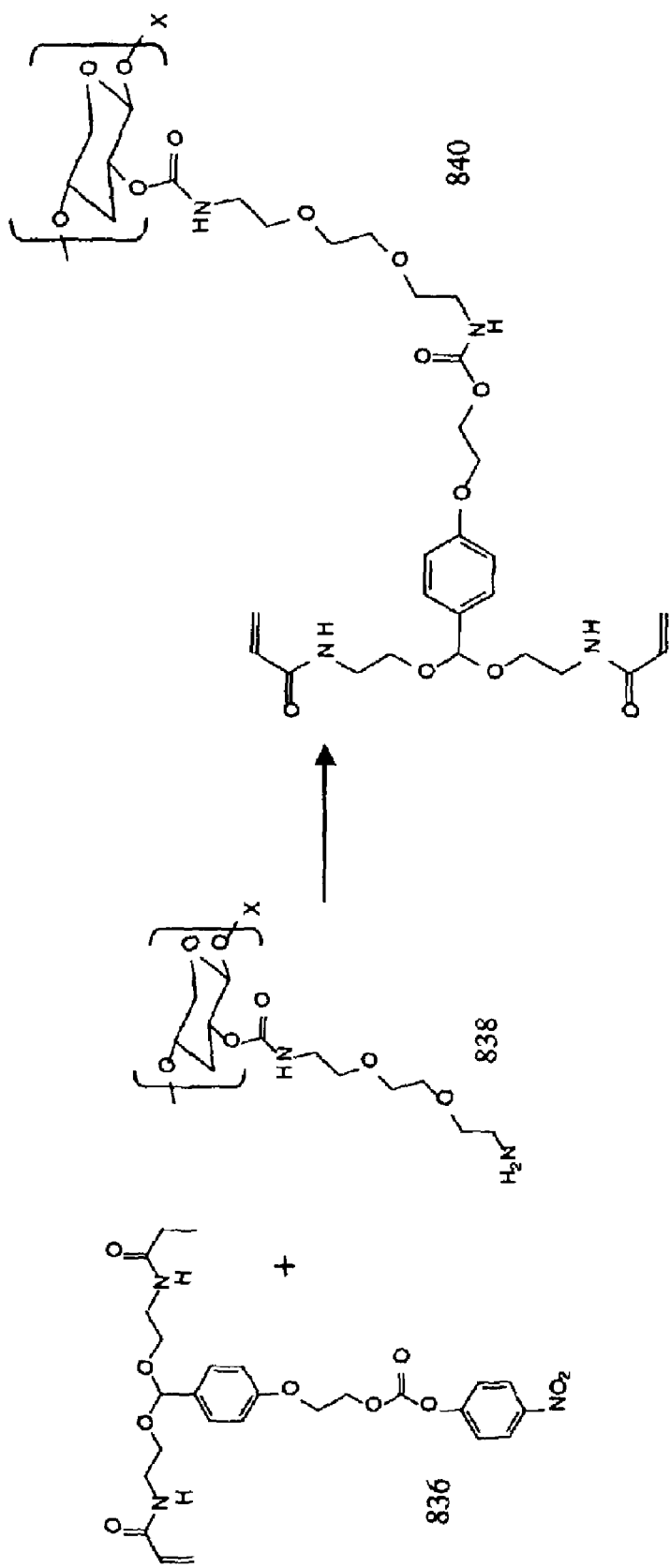
FIG. 8B shows the conjugation of the crosslinker 836 with activated dextran to yield a dextran acetal crosslinker 840.

Dextran microgel particles were made using the bisacrylamide nitrochloroformate acetal crosslinker 836 of Example 8 using inverse microemulsion polymerization as described in Example 7. Referring now to FIG. 8B, the bisacrylamide nitrochloroformate acetal crosslinker 836 was modified to the dextran acetal crosslinker 840 by introducing an amine handle on dextran and then reacting this activated dextran 838 with the crosslinker 836. The amine was introduced onto the dextran by activating the dextran hydroxyls with para-nitrochlorofomate and then reacting it with diamino-diethylene glycol. $^1$H-NMR indicated that 1 out every six hydroxyls were functionalized with the amine handle. The purification of the dextran products was performed by precipitating the reaction in ethanol. The final dextran acetal crosslinker 840 was synthesized by reacting the amine functionalized dextran 838 with the crosslinker 836, the product 840 was purified by precipitation in ethanol and size exclusion chromatography. H-NMR and U.V. spectroscopy indicated that approximately 1 out 6 of the sugars reacted with the crosslinker 836.

Figure 8C:
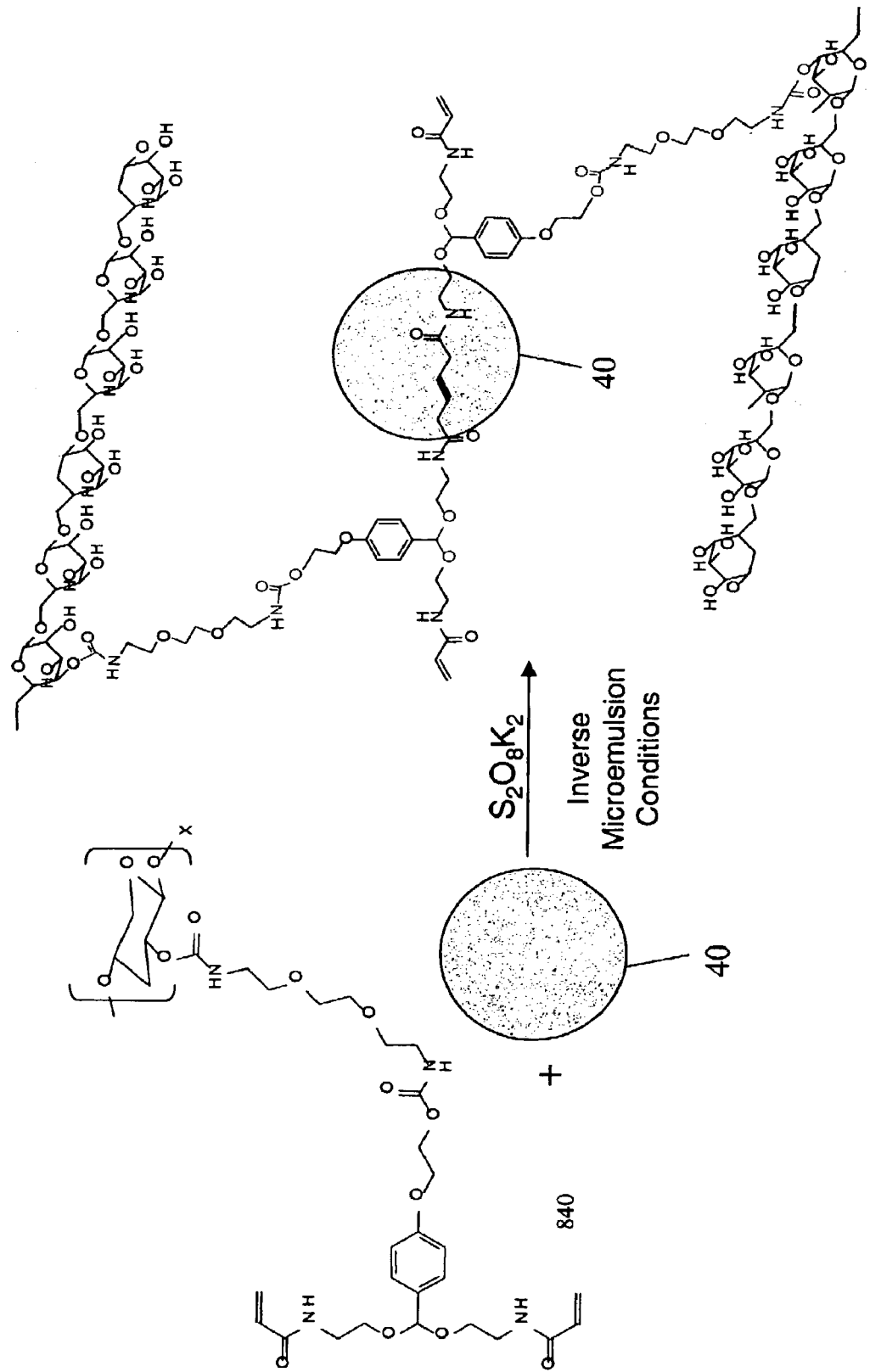
FIG. 8C shows synthesis of dextran microgels using crosslinker 840.
Figure 10:
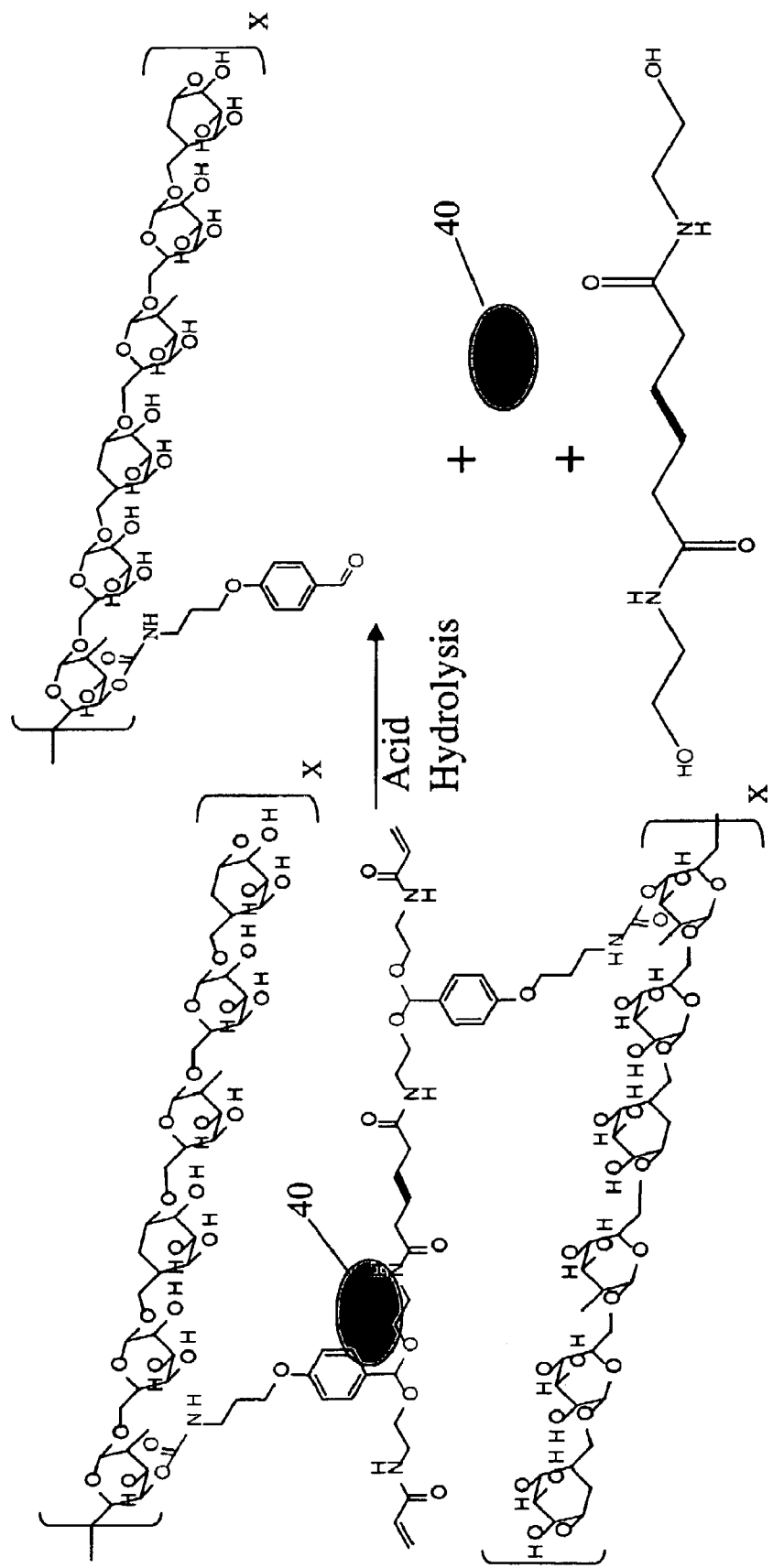
FIG. 10 is a schematic showing dextran microgels upon acid hydrolysis and biodegredation.
Figure 11:
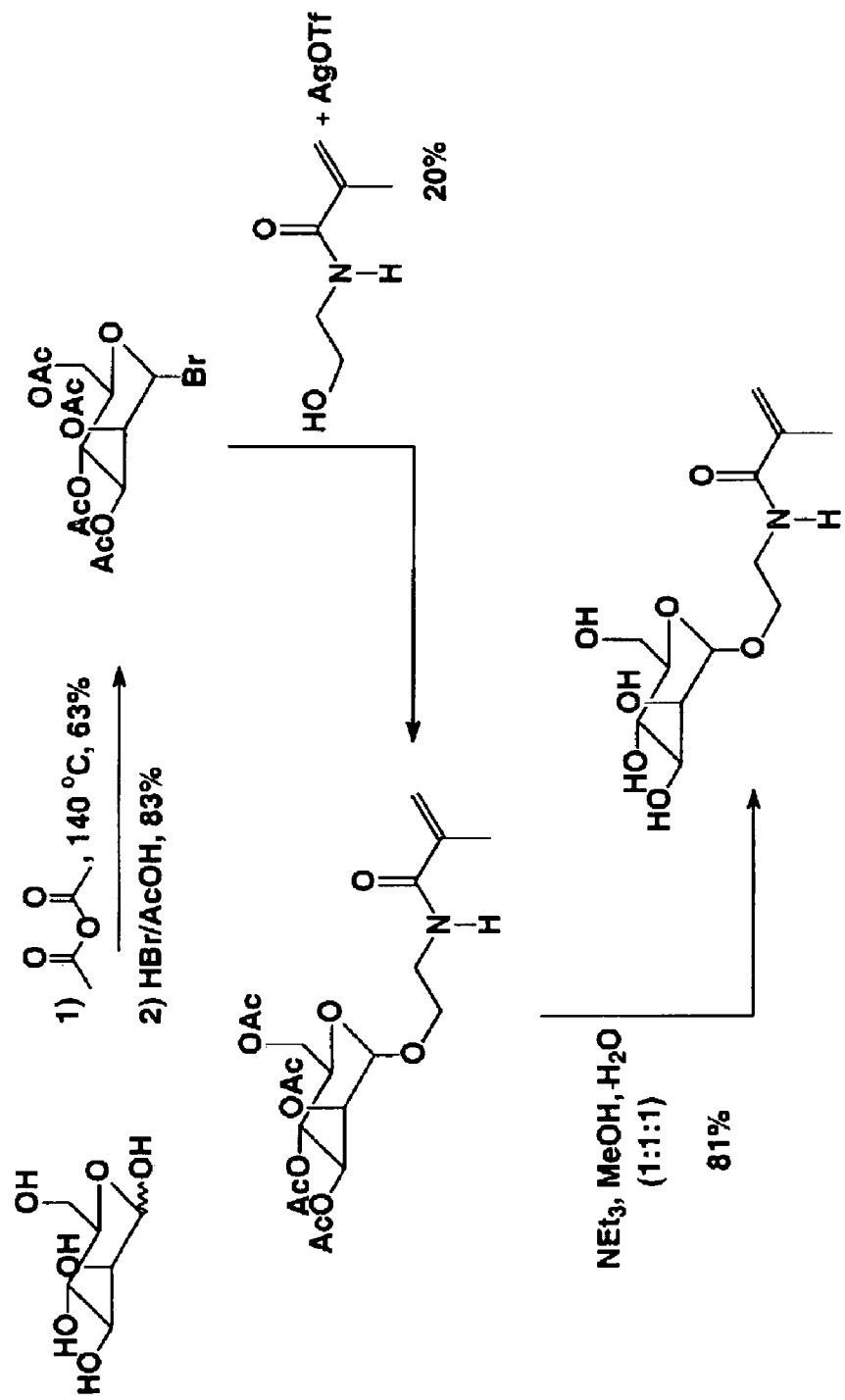
FIG. 11 is a schematic showing the synthesis to activate mannose to incorporate immunostimulatory groups such as mannose into microgels to increase CTL activation.

Referring now to FIG. 8C, dextran microgels were made under inverse microemulsion polymerization conditions using SPAN 80/TWEEN 80 as surfactants and hexane as the oil phase. Upon addition of $S_2O_8K_2$ (potassium persulfate), 300 mg of the bisacrylamide-dextran-acetal crosslinker 840, in the presence of 1 mg DNA, copolymerized to entrap the DNA and formed loaded dextran microgels which are biodegradable as shown in FIG. 10. An SEM image of the microgels showed that the shape of the dextran microgels are not spherical, but nevertheless are individual microparticles. The number of dextran molecules in this example (X in FIG. 8B) should preferably be between 3 to 555 sugar molecules, with a MW of no more than 100,000.

EXAMPLE 10

Synthesis of Bisacrylamide-Dextran-Acetal Crosslinker

A bisacrylamide-dextran-acetal crosslinker 920 can be synthesized by the synthesis steps as shown in FIGS. 9A–9B. Referring now to FIG. 9A, hydroxy benzaldehyde 902 is reacted with 1,3 bromo-propyl-chloride in the presence of $K_2CO_3$, 18-6 Crown Ether, and THF, resulting in benzaldehyde-4-methoxy-propyl chloride 844 at 30% yield. The azide is formed by reacting compound 904 with $NaN_3$, DMF at 90–100° C., yielding azidopropyl benzaldehyde 906 in 70% yield. The acetal linkage is made by reacting the second intermediate, azidopropyl benzaldehyde 906, with (2) molecules of hydroxy-ethyl trifluoroacetamide, in the presence of p-toluenesulfonic acid, THF, using 5 A molecular sieves to yield the bistrifluoroacetamide methoxyphenyl-propyl-azide-acetal 908 at 49% yield. This intermediate azide-acetal 908 is then reduced to an amine acetal by $PPh_3$, THF, TEA, $H_2O$ to yield a bistrifluoroacetamide amine acetal 910.

Referring now to FIG. 9B, the bistrifluoroacetamide amine acetal 910 is then reacted with para-nitrochloroformate-activated dextran 914 in DMSO to yield a dextran-trifluoroacetamide acetal. The activated dextran 914 is prepared as described in Example 9, wherein an amine handle on dextran was introduced to produce activated dextran 838. The amine was introduced onto the dextran by activating the dextran hydroxyls with para-nitrochlorofomate and then reacting it with diamino-diethylene glycol. $^1$H-NMR indicated that 1 out every six hydroxyls were functionalized with the amine handle. The purification of the dextran products was performed by precipitating the reaction in ethanol. The product is then purified by ether/ethanol precipitation and gel permeation chromatography to yield a bistrifluoriacetamide-dextran-acetal 916.

Referring now to FIG. 9C, after purification, the bisacrylamide dextran acetal 920 was synthesized in two steps by first reacting the bistrifluoriacetamide-dextran-acetal 916 with $K_2CO_3$, MeOH and $H_2O$ to yield a bisamine-dextran-acetal 918. The addition of pyridine and pH 10 buffer in the presence of acryloyl chloride to maintain pH then yields a bisacrylamide-dextran-acetal crosslinker 920.

Refering now to FIG. 9D, dextran microgels can be made using the inverse microemulsion polymerization conditions of Example 7. Upon addition of a radical source like potassium persulfate to the bisacrylamide dextran acetal crosslinker 920 in the presence of bioactive materials, the crosslinker will polymerize and trap the bioactive material 40 and form loaded dextran microgels which are biodegradable as shown in FIG. 10.

The number of dextran molecules attached should preferably be between 3 to 555 sugar molecules, with a MW of no more than 100,000.

EXAMPLE 11

Increased Protein Loading

The bisacryloyl acetal crosslinker used to synthesize acid degradable protein loaded microgels influences the loading efficiency of the microgels. The bioactive material is physically entrapped in the microparticle by polymerizing the polymerizable groups and crosslinker in the presence of the bioactive material. A key parameter in the synthesis of protein-loaded microgels is their "pore size", which needs to be smaller than the radius of the protein or other bioactive material for efficient encapsulation.

Ovalbumin was chosen as the model protein for the encapsulation studies because numerous immunological assays have been developed for this protein. Ovalbumin labeled with Cascade Blue was encapsulated in microgels containing 1.6, 3.5 and 12.8 mole percent of bisacrylamide triglyme-acetal crosslinker 606. The results of the protein encapsulation experiment are listed in Table 1, with protein loadings varying from 9–11 µg of protein per mg of microgel. Based on the starting protein/monomers ratio, this represents about 50% encapsulation efficiency.

Protein Encapsulation Measurements. 2 mg of each microgel particle sample (see Table 1), containing Cascade Blue labeled Ovalbumin, was dispersed in 0.5 mL of pH 8.0 300 mM sodium phosphate buffered water by sonication for 5 minutes. The microgel samples were centrifuged for 5 minutes and the supernatant was pipetted off to remove any unbound protein. The washed microgels were then hydrolyzed in 300 mM sodium acetate buffered water (pH 1.6, 500 µL). After complete hydrolysis of the microgel particles, the quantity of encapsulated protein was determined by fluorescence spectroscopy, excitation at 405 nm, emission at 460 nm. The protein concentration of each microgel sample was calculated by fitting the emission to a calibration curve made from known concentrations of Cascade Blue labeled Ovalbumin. The loading efficiency measurements may be lower than actual amount because there may protein entrapped in microgels that do not centrifuge down and thus cannot be recovered.

The encapsulation efficiency obtained with the bisacrylamide triglyme-acetal crosslinker was similar to that observed by others for the encapsulation of ovalbumin in non-degradable microgels composed of 2.5 mole percent methylene bisacrylamide and 97.5 mole percent acrylamide (O'Hagan, D. T.; Palin, K.; Davis, S. S.; Artursson, P.; Sjoholm.; *Vaccine*. 1989, (7), 421–424. ). The encapsulation efficiency of the microgel particles made with the bisacrylamide triglyme-acetal crosslinker did not change appreciably with the crosslinking ratio as shown by the amounts of encapsulated albumin per mg of microgel particle (µg/mg) in Table 1. This lack of correlation between crosslinking ratio and protein encapsulation has been previously observed by Ekman et al. for the encapsulation of human serum albumin in non-degradable microgels composed of methylene bisacrylamide and acrylamide (Ekman, B. et al., (1976) *Biochemistry* 15, 5115–5120).

TABLE 1

| Sample | Mole Percent Cross-linking | Cross-linker (mg) | Acryl-amide (mg) | Cascade Blue Labeled Albumin (mg) | Encapsulated Albumin/ Particle Wt. (µg/mg) | Wt. % Yield of micro gels |
|---|---|---|---|---|---|---|
| A | 1.6 | 25 | 225 | 5.4 | 10.4 | 38.0 |
| B | 3.5 | 50 | 200 | 5.7 | 11.1 | 61.0 |
| C | 12.8 | 125 | 125 | 5.4 | 9.5 | 43.0 |

The protein loading efficiency of the gel particles polymerized with 1.6% crosslinking with the bisacrylamide triglyme-acetal crosslinker 606 of Example 4 was compared to the protein loading efficiency of the microgel particles polymerized with the 1.6% of the bisacrylamide tetraglyme-acetal crosslinker 710 of Example 5. The crosslinkers were copolymerized with acrylamide in a PBS buffer containing the fluorescently labeled protein FITC-Albumin (1 mg/ml). Table 2 lists the resulting amount of ovalbumin encapsulated per milligram of microgel particles.

TABLE 2

| Cascade Blue-Albumin in Polymerization (mg) | Triglyme Encapsulated Albumin/Microgels (µg/mg) | Tetraglyme Encapsulated Albumin/Microgels (µg/mg) |
|---|---|---|
| 21.0 | 9.5 | 44.3 |
| 67.2 | 22.0 | — |
| 133.0 | 62.6 | 135.6 |
| 183.9 | — | 154.8 |

EXAMPLE 12 pH Dependant Release of Encapsulated Bioactive Material by Hydrolysis

The bisacrylamide triglyme acetal crosslinker 606 was used to synthesize acid degradable protein loaded microgels according to the conditions described in Example 7. 2 mg of each microgel sample from Table 1 containing Cascade Blue labeled Ovalbumin was dispersed in 0.5 mL of pH 8.0 300 mM sodium phosphate buffered water by sonication for 5 minutes. The microgel samples were centrifuged for 5 minutes and the supernatant was pipetted off to remove any unbound protein. The recovered pellet was then redispersed into either 300 mM acetic acid buffered water (pH 5.0, 500 µL) or 300 mM sodium phosphate buffer (pH 7.4, 500 µL). The solutions were incubated at 37° C. in a heating block for each time point. The percentage of protein released at a given time point was determined by centrifuging the microgel sample for 5 minutes, isolating the supernatant from the pellet and comparing the fluorescence of the supernatant (released protein) with that of the pellet (protein still in microgels), excitation at 405 nm, emission at 460 nm. The recovered pellet was hydrolyzed in pH 1.6 300 mM acetic acid, before measuring its fluorescence. The background emission of each buffer was measured and subtracted from all of the readings.

The release of protein from the microgels was measured at pH 5.0 and 7.4 to understand their behavior in the environments of the phagosome and blood, respectively (data not shown). Microgels made with bisacrylamide triglyme acetal crosslinker 606 release their contents much faster at pH 5.0 than at pH 7.4. For example, at pH 5.0, after 5 hours, the 1.6% crosslinked microgels released 80% of encapsulated ovalbumin, whereas at pH 7.4, only 10% was released. This pH dependency is caused by the acid sensitivity of the crosslinker, which hydrolyzes rapidly at pH 5.0, thus increasing the effective "pore size" of the microgels and the diffusion rate of proteins out of the microgels. In contrast, at pH 7.4, the bisacrylamide triglyme acetal crosslinker remains intact and the majority of encapsulated proteins are retained. A small percentage of encapsulated proteins are initially released at pH 7.4. This is likely due to the vigorous vortexing and sonication procedures used to disperse the microgel particles, which could dislodge proteins loosely entrapped within the particles.

EXAMPLE 13

Class I Antigen Presentation Assays

The LacZ MHC Class I antigen presentation assay, as described by Sanderson, S.; Shastri, N. in Inter. Immun. 1994, 6, 369–376, was performed with the microgel particles made with the bisacrylamide tetraglyme acetal crosslinker 710 to test their ability to deliver proteins into APCs for Class I antigen presentation. This experiment uses the LacZ B3Z hybridoma, which is a CTL that recognizes the peptide sequence, SIINFEKL, from ovalbumin, complexed with the MHC Class I molecule H-2K$^b$. This hybridoma produces β-galactosidase after encountering APCs that present SIINFEKL as a Class I antigen, thus allowing Class I antigen presentation to be quantified by measuring β-galactosidase activity.

A proper control would be to compare the amount presented by cells when incubated with the SIINFEKL peptide which is directly displayed on the antigen presenting cells and not delivered to the cytoplasm of the cells first. A maximum absorbance of 0.25 is observed with the SIINFEKL peptide, which results in 100% T-cell activation. At about 0.4 mg of particle/mL, the particles made with a 1:1 ratio of acrylamide to the bisacrylamide tetraglyme crosslinker of Example 5, shows an absorbance close to that of 0.25 at which 100% T-cell activation occurs.

The results of the Class I antigen presentation assay show that greater T-cell activation is seen for albumin loaded particles vs. free protein. APCs incubated with free ovalbumin are not able to activate CTLs, indicating that these APCs are unable to present free ovalbumin as a Class I antigen. This is presumably because ovalbumin endocytosed by the APCs, is sequestered in lysosomes, and does not have access to the APC cytoplasm. In contrast, APCs incubated with ovalbumin encapsulated in the microgel particles, can efficiently activate CTLs. Ovalbumin encapsulated in the microgels is several orders of magnitude more efficient than free ovalbumin at inducing the activation of CTLs, for example, 1 µg/ml of ovalbumin encapsulated in the microgels gives T cell activation levels that are 3 times greater than 1 mg/ml of free ovalbumin (the U.V. absorbance resulting from activation with 1 mg/ml of free ovalbumin was only 0.037 versus 0.1106 for activation with 1 µg/mL of ovalbumin encapsulated in the microgels). Thus the acid degradable microgels are capable of delivering protein antigens into APCs for Class I antigen presentation.

Higher protein loading was shown to lead to an increase in antigen presentation. For example, the absorbance taken for 0.1 mg particle/mL of particles, made with the biscarylamide triglyme acetal crosslinker of Example 4, having a protein loading capacity of 22 µg protein/mg of particle, is close to the same absorbance for 0.5 mg particle/mL of particles, made with the same but greater percentage of crosslinker, and having a 9.5 µg/mg loading capacity. There may be a point where there is a maximum level of antigen presentation as shown by the same absorbance of about 0.33 with 0.5 mg/mL of particles having 22.0 and 62.6 µg protein/mg of particle loading capacity. In contrast the biscarylamide tetraglyme acetal crosslinker of Example 5 has a 135.6 µg/mg loading capacity and an absorbance of 0.38, which is almost twice the absorbance of the SINFEKL peptide in this antigen presentation assay.

EXAMPLE 14

Toxicity of Microgels Made with Bisacrylamide Acetal Crosslinker

The toxicity of bioactive material loaded microgels was measured with the yellow tetrazolium salt, 3-(4,5-dimethylthiazolyl-2)-2,5-diphenyltetrazolium bromide (MTT), assay using RAW 309.CR1 macrophage cells (ATCC No. TIB-69, American Type Culture Collection, Manassas, Va.). The cells are incubated with microgel particles in DMEM media with 10% F.B.S. The microgels were aspirated from the cells, and they were then washed several times with PBS and allowed to grow for 24–48 hours. The cell viability is determined by measuring the absorbance of the reduced MTT reagent using the protocol described in Freshney et al. (Freshney, I. R. (1994) *Culture of animal cells*, Wiley-Liss, Inc, New York, N.Y.) as compared to a control. MTT (yellow) is reduced metabolically by healthy cells in part by the action of dehydrogenase enzymes in mitochondria, to generate purple formazan crystals, which are solubilized by the addition of a detergent and the absorbance is measured at 570 nm. Thus, the measurement of the ability of cells to reduce the MTT reagent metabolically is a measurement of the health of the cell population.

RAW 309.CR1 macrophage cells were split at $5 \times 10^4$ cells per well in a 96 well plate and allowed to grow overnight. The cells were then incubated with the microgel particles (1.6% crosslinked, sample A from Table 1 in Example 11) with variable amounts of loaded ovalbumin for 24 hours in DMEM media with 10% F.B.S. The microgels were aspirated from the cells, and they were then washed several times with PBS and allowed to grow for another 24 hours.

The cell viability was determined by measuring the absorbance of the reduced MTT reagent. The MTT assay was performed using 0.5, 1, 2.5 and 5 mg particles/mL serum in each well with a microgel loading of 10 micrograms protein/mg microgel particle. After 24 hours, there were almost 100% viable cells remaining in the 0.5 mg particles/mL, 90% viable cells remaining in the 1 mg protein/mg particles, about 80% viable cells remaining in the 2.5 mg particles/mL, and about 80% viable cells remaining in the 5 mg particles/mL. Thus, it can be found that the microgels of the invention are not toxic to mammalian cells because more than 50% of the cells remain viable.

The effect of variable amounts of crosslinking on viability of cells was also observed. RAW 309.CR1 macrophage cells were split at $5 \times 10^4$ cells per well in a 96 well plate and allowed to grow overnight. The cells were then incubated with the microgel particles made with the bisacrylamide tetraglyme acetal crosslinker (1.6% crosslinked, 9:1 ratio, sample A and 12.8% crosslinked, 1:1 ratio sample C from Table 1 in Example 11) with variable amounts of loaded oavalbumin for 20 hours in DMEM media with 10% F.B.S. The particles were aspirated from the cells, and they were then washed several times with PBS and allowed to grow for another 24 hours.

The MTT assay was performed using 0.5, 1, 2.5 and 5 mg protein/mL serum in each well with a particle loading of 10 micrograms protein/mg microparticle After 24 hours, cells incubated with the particles having 12.8% crosslinker showed 80% viable cells remaining after exposure to 0.1 mg/mL of particles, 74% viable cells remaining in 0.5 mg/mL particles, 62% viable cells remaining in 1.0 mg/mL particles, 63% viable cells remaining in 2.5 mg/mL particles, and 47% viable cells remaining in 5 mg/mL particles. After 24 hours, cells incubated with the particles having 12.8% crosslinker showed 70% viable cells remaining in 0.5 mg particles/mL, 63% viable cells remaining in 0.5 mg particles/mL, 62% viable cells remaining in the 1 mg protein/mg particles, about 62% viable cells remaining in the 1 and 2.5 mg protein/mL particles, and about 52% viable cells remaining in the 5 mg protein/mL particles.

EXAMPLE 15

Cytoplasmic Release of Bioactive Material from Microgels

Microgel particles were made with acrylamide and bisacrylamide triglyme acetal crosslinker 606 encapsulating fluorescently labeled dextran (because it easier to label and observe than fluorescence-labeled DNA) and fed to macrophage cells. When a bisacrylamide methylene nondegradable crosslinker is used, the fluorescence is more localized showing that when nondegradable microgels have been taken up by the cells, they remain sequestered in the lysosome without a mechanism of release. When the acid degradable bisacrylamide triglyme acetal crosslinker is used to make the microgels, the fluorescence is more diffuse within the cytoplasm of cells, which is indicative of cytoplasmic release of the microgel contents.

EXAMPLE 16

Excretion of Degraded Particles

Polymers with high MW are not easily excreted from body, therefore another aspect of the invention is to make microgel particles that easily and safely excreted by the body after being degraded in the acidic cellular compartment. Light scattering results in Table 3 showed the following for microgel particles made without protein after hydrolysis and purification by dialysis with a minimum size of 13,000 MW as a cutoff size:

TABLE 3

| Crosslinking Mole Ratio | dn/dc | Mw |
| --- | --- | --- |
| 9:1 acrylamide/triglyme crosslinker | 0.177 | 498,000 |
| 1:1 acrylamide/triglyme crosslinker | 0.169 | 604,000 |

Referring now to FIG. 10, in a preferred embodiment, dextran microgel particles were made according to Example 9 using the crosslinker of Example 8. After degradation of the microgels, (activated) dextran of 10,000 MW is easily secreted from the body and should exhibit no toxicity problems because it is a sugar. The bioactive material 40 is released along with the linker group upon hydrolysis.

However, one aspect of using dextran microgels that was observed is that protein loading must be about 10 μg protein/mg particle before the antigen presentation assay of Example shows absorbance of 0.25 which is the target absorbance at which there is 100% T-cell activation. Dextran microgel particles also enhance antigen presentation versus free protein but about ⅓ as efficient as using acrylamide as the polymerizing group. One other concern with dextran microgels is the dispersability of the particles in solution because dextran may not be sufficiently hydrophilic.

EXAMPLE 17

Gel Particles Encapsulating Plasmid DNA

Synthesis. Synthesis of gel particles encapsulating plasmid DNA was as follows. Plasmid DNA (pSV-β-gal vector, 6820 bp, Amp resistant) is added directly to the aqueous phase of an inverse microemulsion. The procedure is directly analogous to that for the protein loaded microgel particles made in Example 7. The organic phase consisted of hexane with 3% of the surfactants: 3/1 SPAN 80/TWEEN 80. Acrylamide monomer and the bisacrylamide triglyme acetal crosslinker (in a 4/1 mass ratio), potassium persulfate, and 250 ng plasmid DNA were dissolved in 300 mM PBS, pH 8.0. The two phases are combined and sonicated for 30 sec, at which point, TMEDA (tetramethylethylenediamine) was added, and the polymerization allowed to proceed for 10 min. The microgels were collected by centrifugation (10 min×3000 RPM) and washed once with hexane and twice with acetone, then dried under vacuum overnight.

Loading Efficiency. To examine the loading, the microgels were suspended in pH 7.4 buffer (300 mM PBS) to a concentration of 5 mg/mL. They were then collected by centrifugation, and the supernatant was removed by pipet. This step serves to remove any DNA that is adsorbed to the surface of the microgels but is not actually incorporated inside. The microgels were then taken up in pH 5.0 buffer (300 mM acetic acid) and incubated at 37° C. overnight for 12–18 hours. The acidic pH of the buffer cleaves the acetal linkage in the crosslinker moiety, producing linear polymer chains and free DNA. The plasmid DNA was then quantified by fluorescence using PICOGREENTM intercalation (Molecular Probes, Eugene, Oreg.), a fluorescent dye that binds only double stranded DNA.

About 50% of the DNA that was originally loaded was encapsulated by the microgels. Table 4 shows the estimated loading efficiency of the microgels made with the bisacrylamide triglyme acetal crosslinker. The highest amount loaded was 4 µg DNA/mg of linear polymerizing group, however, the maximum amount of DNA that can be loaded into a sphere has not yet been reached.

TABLE 4

| Estimated Loading | Supernatant Concentration (µg/mL) | Loading µg DNA/mg microgel) | Efficiency of encapsulation |
| --- | --- | --- | --- |
| 2 µg DNA/mg bead | 1.39 | 0.88 | 44% |
| 4 µg DNA/mg bead | 1.31 | 2.14 | 53% |
| 8 µg DNA/mg bead | 1.87 | 4.29 | 54% |

Analysis of Released DNA. There are three forms of plasmid DNA, which is normally circular: 1) supercoiled, where the circular plasmid is further coiled; 2) open circular, where the plasmid has become untwisted but is still circular; and 3) linear. Open circular and supercoiled plasmid DNA both undergo transcription. When digested with HindIII and XmnI restriction enzymes, the plasmid is cut twice into portions of 2263 bp and 4557 bp. The control was the plasmid DNA before transformation of DH5α$E.$ $coli.$ After hydrolytic release from the gel particles the DNA was subjected to a restriction digest with HindIII and XmnI and then analyzed by gel electrophoresis (0.7% agarose, 50V for 150 minutes) and post stained with ethidium bromide (gel not shown). The lanes of control and released DNA subject to the double digest looked identical with some linear single cut plasmid still present. Prior to encapsulation, the DNA is mostly supercoiled (lower band at 4361 bp) with some open circular. After sonication, vacuum drying, and exposure to acidic solution for 18 hours, the DNA is mostly open circular with some linear and supercoiled structures.

Supercoiled and open circular plasmid DNA are still able to undergo transcription in cells but linear DNA cannot. When DNA is isolated from bacteria and loaded into the microgels, the DNA was mostly supercoiled. When isolated from the microgels, the DNA was mostly open circular, with some linear and some supercoiled structure. The DNA at this point had been through three major reaction conditions: sonication, radical polymerization, and acid exposure (pH 5, 37° C., 18 h). It is quite remarkable that that the DNA remained intact because sonication of naked DNA is known to shear and break it into linear strands or fragments. DNA is known to withstand acidic conditions, but it is rare to observe any kinetics after exposure to an acidic pH for such an extended period of time. The restriction digest (single and double cut) serves to give a footprint, demonstrating that the DNA that was encapsulated and went in to the polymerization had the same footprint as the DNA that was recovered.

Toxicity of DNA Encapsulated Microgel Particle. The microgels were tested for toxicity using the MTT assay of Example 14. RAW 309.CR1 macrophage cells were split at $5 \times 10^4$ cells per well in a 96 well plate and allowed to grow overnight. The cells were then incubated with the microgel particles (1.6% crosslinked, sample A from Table 1 in Example 11) with variable amounts of loaded DNA for 16 hours in DMEM media with 10% F.B.S. The particles were aspirated from the cells, and they were then washed several times with PBS and allowed to grow for another 48 hours.

The cell viability was determined by measuring the absorbance of the reduced MTT reagent. The MTT assay was performed using 5 mg microgels/mL serum in each well with a particle loading of 0, 1, 2 and 4 µg DNA/mg microgels. After 48 hours, there were 82% viable cells remaining in the empty microgels, 70% viable cells remaining in the 1 µg DNA/mg microgels, 75% viable cells remaining in the 2 µg DNA/mg microgels, and 65% viable cells remaining in the 4 µg DNA/mg microgels. The concentration tested (5 mg microgels/mL serum) is quite high for most applications, so a toxicity of 80% viability is permissible. It can be concluded that neither the polyacrylamide microgels nor the DNA is toxic to the macrophage cells because at least 50% viable cells are left.

The microgel particles were also tested for DNA release. The microgel particles were suspended in either pH 7.4 or pH 5.0 buffer. The amount of DNA released into the supernatant was quantified by fluorescence using PICOGREEN™ (Molecular Probes, Eugene, Oreg.). At pH 7.4, there is an initial burst, as is also seen with the protein loaded microgel particles in Example 12. This is most likely due to DNA that is adsorbed onto the surface. At pH 5, all of the DNA is readily released within two hours. The microgels are visually degraded after 30 min and appear as a gel in this assay after hydrolysis.

EXAMPLE 18

Evaluation of DNA Released from Microgels

Because the plasmid DNA is physically entrapped within the microgel particles made with the bisacrylamide triglyme acetal crosslinker, the DNA is protected from otherwise being degraded in the serum. DNase enzymes readily chew up naked DNA in serum, however the encapsulated DNA showed good stability. The microgels were incubated in serum (90% DMEM, 10% FBS) for a set period of time of 24 hours. The microgels were then collected, and the serum supernatant removed. The plasmid DNA was isolated from the microgel particles by placing in acetic acid for 6 hours at, pH 5.0. Following hydrolysis of the microgels, the DNA released was quantified using PICOGREEN™. The DNA is fully protected from enzymes in the serum as shown by the fact that transfection is still possible with the recovered DNA.

The recovered DNA from the gel particles was tested for its viability by transfecting cells. Kidney 293T cells (ATCC, Manassas, Va.) is a kidney cell line, relatively easy to transfect. The 293T cells are treated with DNA and Lipofectamine 2000 (Promega, Madison, Wis.), a cationic lipid, a known transfection agent. If the DNA that is recovered is intact, the cells should produce β-galactosidase upon transfection. After 24 h, the cells were lysed and a galacto-orthonitrophenol substrate was added. β-galactosidase is present, the acetal bond in galacto-ortho-nitrophenol is cleaved and the released phenolate turns purple and absorbs at 570 nm.

The addition of plasmid DNA alone to the cells causes no transfection and no β-galactosidase activity is detected. Cells that were transfected by the control plasmid DNA showed an absorbance of 0.55, 0.6 and 1.0 at DNA concentrations of 0.25 ng, 0.50 ng and 1.0 ng. Cells transfected with open circular DNA isolated from the microgel particles also shows β-galactosidase activity and had absorbances of 0.4 and 0.55 at 0.25 ng and 0.50 ng respectively.

However, no transfection is observed with RAW cells, macrophages, either with the known control plasmid DNA or with the DNA isolated from the microgel particles, likely because macrophages are very difficult to transfect.

EXAMPLE 20

Evaluation of Immune Response to DNA Released from Microgel ParticlesPlasmid encapsulated microgels were fed to macrophages, and two indicators of immune activity were analyzed by evaluating IL-6 and $NO_2$ levels which are both indicative of an immunistimulatory response.

Interleukin-6 was detected by an ELISA assay. RAW 264.7 macrophages were incubated with either microgels encapsulating plasmid DNA or naked plasmid overnight. The supernatant was analyzed for IL-6 production using an ELISA kit (Pierce Biotechnology, Rockford, Ill.). The IL-6 enzyme levels were detected for the following amounts of DNA added to each well: untreated (control), 1 μg of DNA encoding β-galactosidase, 1 μg plasmid DNA+lipofectamine, unloaded microgels, 0.1 μg plasmid DNA in microgels, 0.2 μg plasmid DNA in microgels, and 0.4 μg plasmid DNA in microgels.

Untreated cells as well as those incubated with plasmid DNA show a low level of about 300–400 μg/mL of secreted IL-6. When DNA was mixed with Lipofectamine 2000, the IL-6 level is increased to about 2000 μg/mL of IL-6. Lipofectamine 2000 (Invitrogen Corporation, Carlsbad, Calif.) is a commercially available transfection agent that forms micelles around the DNA, protecting it from nucleases in the serum and facilitating cellular delivery. Therefore, this shows that naked DNA requires a transfection agent, such as Lipofectamine, in order to produce an immune response.

Unloaded microgels had no IL-6 response, meaning that microgels alone do not induce an immune response. Microgels with DNA did induce IL-6 secretion. When as little as 0.1 μg of DNA is delivered per well, an immune response of about 350 pg/ml of IL-6 is observed. When 0.2 μg of plasmid DNA is delivered in microgels, there is about 1700 pg/mL of IL-6 detected. This is equivalent to a 30-fold increase in IL-6 production when compared to naked DNA alone, for which 1 μg is delivered per well. For a loading in which 0.2 μg of plasmid DNA is delivered per well using the microgels, an IL-6 response of 7 times that of DNA alone was observed where 5 times the amount of DNA is delivered. A higher loading of DNA, 0.4 μg, does not produce a higher response, but a production of 1500 pg/mL IL-6 is observed, indicating that a maximum response was reached for DNA loading.

Macrophages also release other mediators including prostraglandins, oxygen radicals, peroxides, NO, etc. Comparing these same samples again, there was a 70-fold enhancement in NO activity when the DNA is encapsulated in the microgels. Nitric oxide is detected by the Griess assay by measuring $NO_2^-$. RAW 309.1 cells were split onto a 96 well plate at $4 \times 10^5$ cells per well the night before the experiment and grown in 10% serum containing DMEM medium. The medium was then removed and the appropriate microparticle sample was added, and the cells were grown in serum containing media for 16 hours. The media was then aspirated off and the cells were stimulated with 10 units/ml of gamma interferon and 10 μg/ml of LPS for 8 hours in serum containing media (to stimulate $NO_2$ production). The medium was then isolated and the concentration of NO was measured by mixing the supernatant with an equal volume of Griess reagent (1% sulfanilamide, 0.1% naphthylethylene-diamine hydrochloride, and 5% phosphoric acid). The absorbance at 540 nm was measured after 10 minutes at room temperature.

There was no detected NO production for the untreated cells, or the cells incubated with 1 μg of DNA encoding β-galactosidase, unloaded microgels, or 0.1 μg plasmid DNA in microgels. About 14 μM of $NaNO_2$ was detected for cells incubated with 1 μg plasmid DNA+lipofectamine, 15.5 μM of $NaNO_2$ was detected for cells incubated with 0.2 μg plasmid DNA in microgels, and 11 μM of $NaNO_2$ was detected for cells incubated with 0.4 μg plasmid DNA in microgels.

EXAMPLE 21

Test particles with Dendritic Cells in In Vitro and In Vivo Studies

In the in vitro experiment, bone marrow dendritic cells are grown then pulsed with the microgel particles made according to Example 7. Dendritic cells phagocytose antigens and display antigens upon maturation. Therefore these in vitro studies can show that the microgels of the present inventions are effective in delivering bioactive material to dendritic cells which then display them and initiate the innate immune response.

These microgel particles are made with the crosslinkers of Example 4 or 5. The dendritic cells are pulsed at an immature stage and then cultured with ovalbumin (OVA) transgenic CD4 and CD8 T-cells for several days. The following groups can be tested: microgels entrapping OVA, microgels entrapping OVA+TNF, microgels entrapping protein control, microparticles entrapping protein control+TNF, OVA alone, OVA+TNF, and peptide+TNF. The amount of OVA used should be about 50–100 μg/ml, which means that approximately 250–500 μg of protein total or less should be entrapped within the microgels. A similar amount of microgels that do not contain OVA or that contains a different protein is required for a control.

In the in vivo experiment the microparticles are injected into the food pad of CD4 or CD8 transgenic mice to show that microgels can activate cytotoxic T lymphocytes in vivo. More preferably, delivery is by injection of 50 μl of resuspended particle using a 25 gauge syringe in the flanks of these transgenic mice. At least 50 μg of OVA/mouse should suffice per injection with at least 3 mice per group injected. Also 150 μg of microgels with OVA and a similar amount of mirogels used for control are injected. The lymph nodes are isolated 7 days after the injection and analyzed for antigen specific T cell priming.

While the present compositions and processes have been described with reference to specific details of certain exemplary embodiments thereof, it is not intended that such details be regarded as limitations upon the scope of the invention, which should be regarded as defined by the following claims.

What is claimed is:

1. An acid hydrolyzable microgel composition, comprising:
   (a) a polymer backbone crosslinked by an acid hydrolyzable crosslinker, wherein said crosslinker hydrolyzes at pH 4.5 to pH 7.4;
   (b) the crosslinker having the formula $R^2CH(OR^1)_2$, wherein
      $R^1$ is an acryloyl group; and
      $R^2$ is Ar—X where X is a water solubilizing group selected from hydrogen, methoxy, —O—($CH_2$—$CH_2$—O)$_n$—$CH_3$ wherein n is from 1 to 10, —O—$CH_2$—$CH_2$—O—C(O)—O—Ph—$NO_2$ and —O—$CH_2$—$CH_2$—$CH_2$ —NH—CO-(dextran polysaccharide), said dextran polysaccharide having a molecular weight from 300 to 100,000 daltons; and Ar is an aryl group;
   (c) a particle size of the microgel composition between 0.1–10 microns; and
   (d) cross linkages between 1 and 20 mole percent.

2. The composition of claim 1 wherein $R^1$ is ethylacrylamide and $R^2$ is such that Ar is phenyl and X is methoxy.

3. The composition of claim 1 wherein $R^1$ is an acrylate, whereby crosslinker hydrolysis causes generation of further acidic species in an autocatalytic manner.

4. The composition of claim 1 wherein the particle size is between 200 nm and 500 nm.

5. The composition of claim 1 wherein said polymer backbone is comprised of a dextran polysaccharide, said dextran polysaccharide having a molecular weight from 300 to 100,000 daltons.

6. The composition of claim 1 further comprising a bioactive material, wherein the bioactive material is selected from the group consisting of palysaccharides, DNA, RNA, amino acids, and proteins.

7. The composition of claim 6 whereby the bioactive material is physically entrapped within the microgel composition.

8. The composition of claim 6 whereby the bioacdve material is adsorbed onto the microgel composition.

9. The composition of claim 6 wherein said bioactive material is an antigen.

10. The composition of claim 6 wherein the bioactive material is unmethylated DNA.

11. An acid hydrolyzable polydextran microgel composition for delivering a bioactive material, comprising:
   (a) a polymerized and crosslinked acid hydrolyzable crosslinker of the formula $R^2CH(OR^1)_2$, wherein said crosslinker hydrolyzes pH 5.0 to pH 7.4,
      wherein $R^1$ is an acryloyl group, and
      $R^2$ is Ar—X where X is an alkyl dextran, wherein said dextran has a molecular weight from 300 to 100,000 daltons; and Ar is an aryl group;
   (b) a particle size of the polydextran microgel composition between 0.1–10 microns; and
   (c) cross linkages between 1 and 20 mole percent.

12. The composition of claim 11 wherein said alkyl-dextran linker has the formula —O—$CH_2$—$CH_2$—O—C(O)—NH—[$CH_2$—$CH_2$—O]$_2$—$CH_2$—$CH_2$—NH —C(O)-dextran, wherein said dextran has a molecular weight from 300 to 100,000 daltons.

13. The composition of claim 11 further comprising a bioactive material, wherein the bioactive material is selected from the group consisting of polysaccharides, DNA, RNA, amino acids, and proteins.

14. The composition of claim 13 whereby the bioactive material is physically entrapped within the microgel composition.

15. The composition of claim 13 whereby the bioactive material is adsorbed onto the microgel composition.

16. The composition of claim 13 wherein said bioactive material is an antigen.

17. The composition of claim 13 wherein the bioactive material is unmethylated DNA.

* * * * *